US012318601B2

(12) United States Patent
Nix et al.

(10) Patent No.: US 12,318,601 B2
(45) Date of Patent: Jun. 3, 2025

(54) ELECTRODE ASSEMBLY PATCH FOR CONDUCTANCE AND ADMITTANCE MEASUREMENTS

(71) Applicant: Abiomed Europe GmbH, Aachen (DE)

(72) Inventors: Christoph Nix, Aachen (DE); Mithun Rajaram, Aachen (DE); Verena Zscherlich, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 511 days.

(21) Appl. No.: 17/496,509

(22) Filed: Oct. 7, 2021

(65) Prior Publication Data

US 2022/0105339 A1 Apr. 7, 2022

Related U.S. Application Data

(60) Provisional application No. 63/252,434, filed on Oct. 5, 2021, provisional application No. 63/173,709, filed
(Continued)

(51) Int. Cl.
*A61M 60/816* (2021.01)
*A61M 60/135* (2021.01)
(Continued)

(52) U.S. Cl.
CPC ........ *A61M 60/816* (2021.01); *A61M 60/135* (2021.01); *A61M 60/216* (2021.01); *A61M 60/523* (2021.01); *A61M 2205/3317* (2013.01)

(58) Field of Classification Search
CPC ................ A61B 5/0215; A61B 5/0538; A61B 2562/125; A61B 5/02007; A61B 5/02028;
(Continued)

(56) References Cited

U.S. PATENT DOCUMENTS 6,494,832 B1 12/2002 Feldman et al.
7,925,335 B2 4/2011 Feldman et al.
(Continued)

FOREIGN PATENT DOCUMENTS

| EP | 3287154 A1 | 2/2018 |
|---|---|---|
| WO | 2019234148 A1 | 12/2019 |
| WO | 2020263962 A1 | 12/2020 |

OTHER PUBLICATIONS

Almomani, et al., "Modification of the Impella Device for Instantaneous Determination of Native Left Ventricular Cardiac Output for Automated Pump Weaning", J Am Coll Cardiol,, vol. 77, No. 18 Supplement 1, p. 591, May 2021.
(Continued)

*Primary Examiner* — Jon Eric C Morales
(74) *Attorney, Agent, or Firm* — Botos Churchill IP Law LLC

(57) ABSTRACT

Electrode assembly patches configured for conductance and admittance measurements, and methods of manufacturing same. The present technology provides designs and manufacturing methods that may enable a conductance or admittance electrode assembly patches to be flexible, low-profile, and easily applied to an intravascular blood pump or other device, such that there may be little or no change to the device's overall diameter, profile, and functionality.

24 Claims, 13 Drawing Sheets

Related U.S. Application Data on Apr. 12, 2021, provisional application No. 63/088,784, filed on Oct. 7, 2020.

(51) Int. Cl.
*A61M 60/216* (2021.01)
*A61M 60/523* (2021.01)

(58) Field of Classification Search
CPC ......... A61B 5/026; A61B 5/027; A61B 5/029; A61B 5/053; A61B 5/14539; A61B 5/1473; A61B 5/287; A61B 5/4836; A61B 5/6848; A61B 5/6855; A61B 5/6869; A61B 5/7235; A61M 2205/3334; A61M 2205/3344; A61M 2205/3379; A61M 60/148; A61M 60/178; A61M 60/216; A61M 60/531; A61M 60/554; A61M 60/857; A61N 1/05; A61N 1/056; A61N 2001/0585
See application file for complete search history.

(56) References Cited

U.S. PATENT DOCUMENTS

| | | | |
|---|---|---|---|
| 9,295,404 | B2 | 3/2016 | Valvano et al. |
| 9,820,673 | B2 | 11/2017 | Feldman et al. |
| 10,076,669 | B2 | 9/2018 | Feldman et al. |
| 10,376,177 | B2 | 8/2019 | Valvano et al. |
| 10,420,952 | B2 | 9/2019 | Feldman et al. |
| 2009/0143651 | A1* | 6/2009 | Kallback ............ A61B 5/287 600/374 |
| 2011/0152661 | A1 | 6/2011 | Feldman et al. |
| 2019/0209755 | A1 | 7/2019 | Nix et al. |
| 2020/0405929 | A1 | 12/2020 | Tan et al. |

OTHER PUBLICATIONS

Bridge Source Medical, "Blood Volume Measurement", obtained Aug. 27, 2021 from the following location: https://www.bridgesourcemedical.com/blood-volume#.

Almomani, Modification of the Impella Device . . . , obtained Aug. 27, 2021, engineering.utsa.edu/makerspace/wp-content/uploads/sites/92/2021/08/Clayton-Foundation-Left-and-Right-Ventricle-Impella-UTSA-Senior-Design-Project-Proposal-2021-0527-with-References.pdf.

Haines, et al., "Validation of a defibrillation lead ventricular volume measurement compared to three-dimensional echocardiography", Heart Rhythm, vol. 14, No. 10, pp. 1515-1522, Oct. 2017.

Holt et al., "A Real-Time Hemodynamic ICD Measurement", JACC: Clinical Electrophysiology, vol. 5, No. 6, pp. 742-743, 2019.

Larson et al., "Analysis of the Spatial Sensitivity of Conductance/Admittance Catheter Ventricular Volume Estimation", IEEE Transactions on Biomedical Engineering, vol. 60, No. 8, pp. 2316-2324, Aug. 2013.

MarcFeldmanMD on Twitter: "Another Great day in Phase 1 with John Porterfield in lab. Murphy's law start but persistence and science . . . ", Jan. 30, 2020.

MarcFeldmanMD on Twitter: "Exciting Result! Phase 1 nearing conclusion. Integrating proven LV volume measurement tech (CardioVol) . . . ", Jan. 15, 2020.

Porterfield, John E., "Native Hemodynamic Measurment as Feedback Cntrol for Mechanical Cardiac Support", obtained Aug. 27, 21 from: https://reporter.nih.gov/search/RYbvJYoLdUWIP8fQlyuh4A/project-details/9774621.

Raghavan, et al., "Electrical Conductivity and Permittivity of Murine Myocardium", IEEE Transactions on Biomedical Engineering, vol. 56, No. 8, pp. 2044-2053, Aug. 2009.

* cited by examiner

700

700

ELECTRODE ASSEMBLY PATCH FOR CONDUCTANCE AND ADMITTANCE MEASUREMENTS

CROSS-REFERENCE TO RELATED APPLICATIONS

The present application claims priority to U.S. Provisional Application No. 63/088,784, filed Oct. 7, 2020, U.S. Provisional Application No. 63/173,709, filed Apr. 12, 2021, and U.S. Provisional Application No. 63/252,434, filed Oct. 5, 2021, the entire disclosures of which are hereby incorporated by reference herein.

TECHNICAL FIELD

The present disclosure relates to electrode assemblies, such as electrode assemblies for intravascular blood pumps.

BACKGROUND

Intravascular blood pumps can be introduced into a patient either surgically or percutaneously and used to deliver blood from one location in the heart or circulatory system to another location in the heart or circulatory system. For example, when deployed in the left heart, an intravascular blood pump can pump blood from the left ventricle of the heart into the aorta. Likewise, when deployed in the right heart, an intravascular blood pump can pump blood from the inferior vena cava into the pulmonary artery. Intravascular blood pumps can be powered by a motor located outside of the patient's body via an elongate drive shaft or by an onboard motor located inside the patient's body. Some intravascular blood pumps can operate in parallel with the native heart to supplement cardiac output and partially or fully unload components of the heart.

BRIEF SUMMARY

The present technology relates to electrode assemblies configured for conductance and admittance measurements, and methods of manufacturing same. In that regard, the present technology describes electrode assemblies adapted for use with intravascular blood pumps and other devices for which real-time ventricular volume measurements may be relevant.

In an embodiment, an electrode assembly patch that is attachable to an intravascular device comprises: a strip extending from a proximal end to a distal end; a first electrode tab extending outwardly and away from the strip, the first electrode tab configured to provide a current to an ambient fluid; a second electrode tab spaced from the first electrode tab, the second electrode tab extending outwardly and away from the strip, the second electrode tab configured to measure voltage in the ambient fluid; a third electrode tab spaced from the second electrode tab, the third electrode tab extending outwardly and away from the strip, the third electrode tab configured to measure voltage in the ambient fluid; and a fourth electrode tab spaced from the third tab, the fourth electrode tab extending outwardly and away from the strip, the fourth electrode tab configured to provide a current to the ambient fluid.

In an embodiment, the first, second, third, and fourth electrode tabs extend outwardly and away from a first side of the strip in a first direction.

In an embodiment, the electrode assembly patch further comprises: a first stabilizing tab extending outwardly and away from a second side of the strip in a second direction opposite the first direction; and a second stabilizing tab spaced from the first stabilizing tab and extending outwardly away from the strip in the second direction.

In an embodiment, the electrode assembly may further comprise a first non-conductive tab extending outwardly and away from the strip; and a second non-conductive tab extending outwardly and away from the strip.

The first and second non-conductive tab may be configured to ensure separation and/or proper alignment of the electrode tabs (when wrapped around an intravascular device).

In addition, or as an alternative, the first and second non-conductive tabs may be configured to enhance adhesion of the electrode assembly patch and may be further configured to stabilize the electrode assembly patch when it is being affixed to a portion of an intravascular blood pump or other device.

The first and second non-conductive tabs may be non-conductive stabilizer tabs.

In an embodiment, the first stabilizing tab is positioned laterally in between the first and second electrode tabs.

In an embodiment, the second stabilizing tab is positioned laterally between the third and fourth electrode tabs.

The second side may be opposite to the first side.

In an embodiment, the electrode assembly patch is configured to be flexible.

The electrode assembly patch may have a sandwich configuration.

The electrode assembly patch may include two or more layers, for example, the electrode patch may include four layers.

The electrode assembly patch may have a multi-layer configuration.

Layers of the electrode patch assembly may be fused or welded together, for example via thermo-forming, or glued together.

The electrode assembly patch may comprise a base layer, for example a non-conductive base layer.

The electrode assembly patch may comprise one or more non-conductive layers and one or more conductive layers.

The base layer may be a non-conductive layer.

The electrode assembly may include an outer layer.

The outer layer of the electrode assembly patch may include one or more exposed electrodes.

In an embodiment, the electrode assembly patch is configured to have a two-dimensional configuration in an undeployed state and wherein the electrode assembly patch is further configured to have a three-dimensional configuration in a deployed state.

For example, the electrode assembly patch can be wrapped or rolled into the three-dimensional configuration.

In an embodiment, each of the first, second, third, and fourth electrode tab includes an electrode extending in the tab.

In an embodiment, the electrode includes one or both of gold or platinum.

In an embodiment, the second tab is spaced apart from the first tab by a first distance, the third tab is spaced apart from the second tab by a second distance, and the fourth tab is spaced apart from the third tab by the first distance.

In an embodiment, the second distance is greater than the first and third distances.

In an embodiment, each of the first, second, third and fourth electrode tabs and each of the first and second stabilizing tabs extend perpendicular to the strip.

In an embodiment a width of the first stabilizing tab is less than or equal to a first lateral distances between the first and second electrode tabs and wherein a width of the second stabilizing tab is less than or equal to a second lateral distance between the third and fourth electrode tabs.

In an embodiment, the electrode assembly patch includes four layers, each layer having a thickness of 5 µm.

In an embodiment, a system for determining an admittance or conductance comprises:
an intravascular device configured to be inserted into a patient's heart; and
a flexible electrode assembly patch attached to at least a portion of the intravascular device, wherein the flexible electrode assembly patch includes two or more electrodes configured to determine an admittance and/or conductance.

In an embodiment, the flexible electrode assembly patch includes: a strip extending from a proximal end to a distal end; a first electrode tab extending outwardly and away from the strip, the first electrode tab configured to provide a current to an ambient fluid; a second electrode tab spaced from the first electrode tab, the second electrode tab extending outwardly and away from the strip, the second electrode tab configured to measure voltage in the ambient fluid; a third electrode tab spaced from the second electrode tab, the third electrode tab extending outwardly and away from the strip, the third electrode tab configured to measure voltage in the ambient fluid; and a fourth electrode tab spaced from the third tab, the fourth electrode tab extending outwardly and away from the strip, the fourth electrode tab configured to provide a current to the ambient fluid.

In an embodiment, the first, second, third, and fourth electrode tabs extend outwardly and away from a first side of the strip in a first direction.

In an embodiment, the system further comprises: a first stabilizing tab extending outwardly and away from a second side of the strip in a second direction opposite the first direction; and a second stabilizing tab spaced from the first stabilizing tab and extending outwardly away from the strip in the second direction.

In an embodiment, the flexible electrode assembly patch includes a strip having a proximal end and a distal end.

In an embodiment, the system further comprises: a controller electrically connected to the electrode assembly patch, the controller comprising: a current source; a memory; and one or more processors coupled to the memory and configured to: provide an alternating current to electrodes of the first electrode tab and the fourth electrode tab; measure voltages through electrodes of the second electrode tab and the third electrode tab; and determine an admittance or a conductance based on the measured voltages of the second tab and the third tab.

In an embodiment, a system for determining an admittance or conductance comprises: an intravascular device configured to be inserted into a patient's heart; and an electrode assembly patch attached to at least a portion of the intravascular device, wherein the electrode assembly patch includes a multi-layered construction comprising: a first non-conductive layer configured to adhered to the portion of the intravascular device; a second layer having one or more wires; a third non-conductive layer configured to electrically insulate the one or more wires; and a fourth layer including one or more electrodes.

In an embodiment, the first non-conductive layer may be formed from a polymer material configured to be glued, bonded and/or thermoformed to the portion of the intravascular device.

In an embodiment, each of the one or more wires are spaced apart by a non-conductive material.

In an embodiment, the one or more wires are formed from a conductive material.

In an embodiment, the conductive material includes platinum, gold, silver, and/or copper.

In an embodiment, the one or more electrodes in the fourth layer are at least partially exposed.

In an embodiment, the multi-layered construction includes four sandwiched layers.

In an embodiment, the layers are glued, bonded, and/or thermoformed together.

In an embodiment, the electrode assembly patch includes: a strip extending from a proximal end to a distal end; a first electrode tab extending outwardly and away from the strip, the first electrode tab configured to provide a current to an ambient fluid; a second electrode tab spaced from the first electrode tab, the second electrode tab extending outwardly and away from the strip, the second electrode tab configured to measure voltage in the ambient fluid; a third electrode tab spaced from the second electrode tab, the third electrode tab extending outwardly and away from the strip, the third electrode tab configured to measure voltage in the ambient fluid; and a fourth electrode tab spaced from the third tab, the fourth electrode tab extending outwardly and away from the strip, the fourth electrode tab configured to provide a current to the ambient fluid.

In an embodiment, the first, second, third, and fourth electrode tabs extend outwardly and away from a first side of the strip in a first direction.

In an embodiment, the system further comprises: a first stabilizing tab extending outwardly and away from a second side of the strip in a second direction opposite the first direction; and a second stabilizing tab spaced from the first stabilizing tab and extending outwardly away from the strip in the second direction.

In an embodiment, the electrode assembly patch includes a strip having a proximal end and a distal end.

In an embodiment, the system further comprises: a controller electrically connected to the electrode assembly patch, the controller comprising: a current source; a memory; and one or more processors coupled to the memory and configured to: provide an alternating current to electrodes of the first electrode tab and the fourth electrode tab; measure voltages through electrodes of the second electrode tab and the third electrode tab; and determine an admittance or a conductance based on the measured voltages of the second tab and the third tab.

In an embodiment, a method of forming a system for determining an admittance or conductance comprises: rolling and/or wrapping a flexible electrode assembly patch to at least a portion of an intravascular device configured to be inserted into a patient's heart; and attaching the flexible electrode assembly patch to the portion of the intravascular device.

For example, it is possible that the cannula of an intravascular blood pump is formed at least partly by the electrode assembly patch.

For example, the cannula may be formed at least partly by rolling and/or wrapping the electrode assembly patch.

The cannula may comprise a support structure and the electrode assembly patch may be rolled and/or wrapped around the support structure.

The support structure may comprise one or more strands or coils of a shape-memory material such as Nitinol.

The electrode assembly patch may form a fluid-tight outer shell of the cannula.

In an embodiment, the step of attaching includes, thermoforming the flexible electrode assembly patch to the portion of the intravascular device.

In an embodiment the flexible electrode assembly patch includes a multi-layered construction.

In an embodiment, the flexible electrode assembly patch includes: a strip extending from a proximal end to a distal end; a first electrode tab extending outwardly and away from the strip, the first electrode tab configured to provide a current to an ambient fluid; a second electrode tab spaced from the first electrode tab, the second electrode tab extending outwardly and away from the strip, the second electrode tab configured to measure voltage in the ambient fluid; a third electrode tab spaced from the second electrode tab, the third electrode tab extending outwardly and away from the strip, the third electrode tab configured to measure voltage in the ambient fluid; and a fourth electrode tab spaced from the third tab, the fourth electrode tab extending outwardly and away from the strip, the fourth electrode tab configured to provide a current to the ambient fluid.

In an embodiment, the first, second, third, and fourth electrode tabs extend outwardly and away from a first side of the strip in a first direction.

In an embodiment, the flexible electrode assembly patch further comprises: a first stabilizing tab extending outwardly and away from a second side of the strip in a second direction opposite the first direction; and a second stabilizing tab spaced from the first stabilizing tab and extending outwardly away from the strip in the second direction.

In an embodiment, wherein the flexible electrode assembly patch includes a two-dimensional configuration before the flexible electrode assembly patch is rolled and/or wrapped onto the intravascular device.

DETAILED DESCRIPTION

Figure 1:
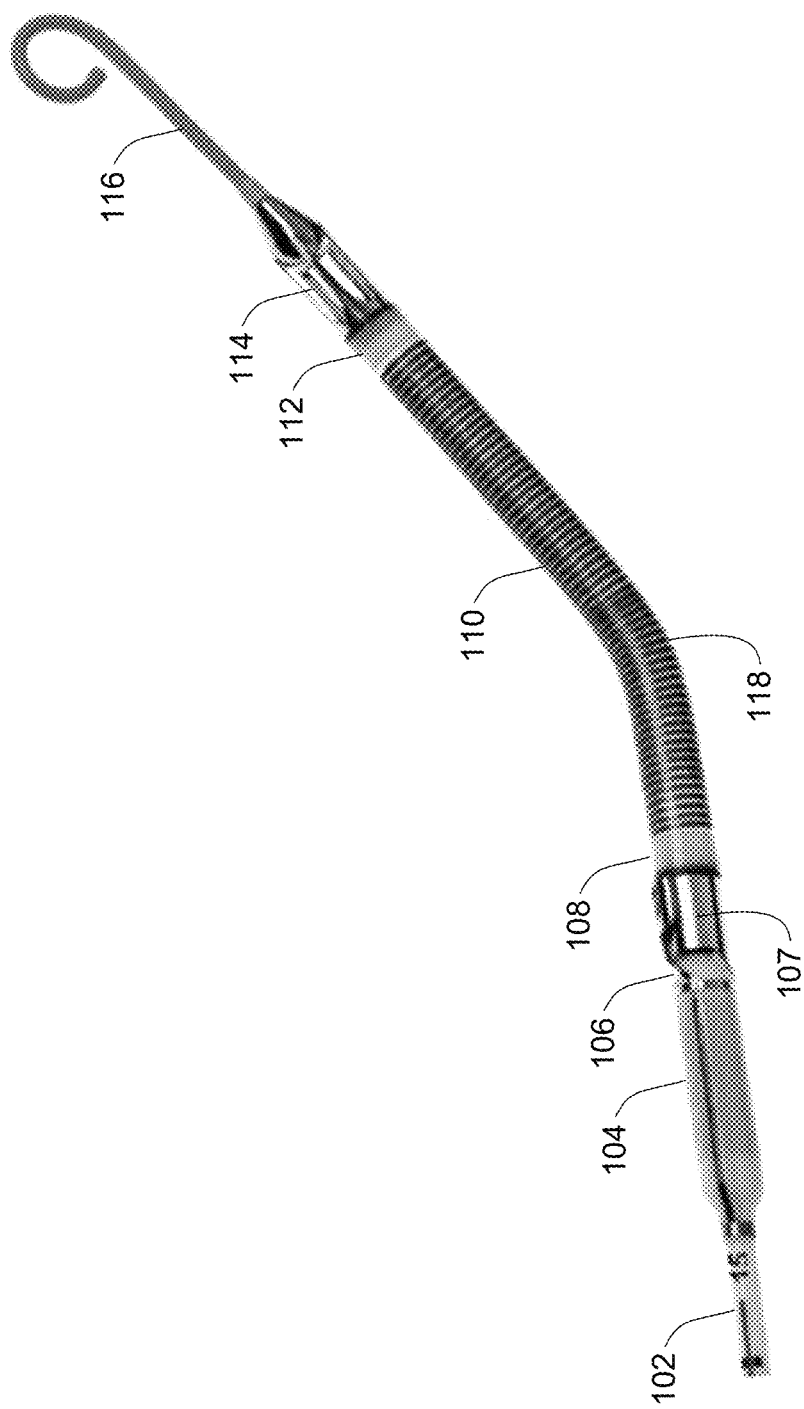
FIG. 1 depicts a schematic perspective view of an exemplary intravascular blood pump configured for left heart support, in accordance with aspects of the disclosure.

Embodiments of the present disclosure are described in detail with reference to the figures wherein like reference numerals identify similar or identical elements. It is to be understood that the disclosed embodiments are merely examples of the disclosure, which may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

To provide an overall understanding of the systems, methods, and devices described herein, certain illustrative examples will be described. Although various examples may describe intravascular blood pumps, it will be understood that the improvements of the present technology may also be adapted and applied to other types of medical devices such as electrophysiology study and catheter ablation devices, angioplasty and stenting devices, angiographic catheters, peripherally inserted central catheters, central venous catheters, midline catheters, peripheral catheters, inferior vena cava filters, abdominal aortic aneurysm therapy devices, thrombectomy devices, TAVR delivery systems, cardiac therapy and cardiac assist devices, including balloon pumps, cardiac assist devices implanted using a surgical incision, and any other venous or arterial based introduced catheters and devices. As is known, intravascular blood pumps can be introduced into a patient, either surgically or percutaneously, to deliver blood from one location in the heart or circulatory system to another location in the heart or circulatory system. For example, when deployed in the left heart, an intravascular blood pump can pump blood from the left ventricle of the heart into the aorta. When deployed in the right heart, an intravascular blood pump can pump blood from the inferior vena cava into the pulmonary artery.

The inventors have recognized the benefits of enabling such intravascular blood pumps to take continuous measurements while the intravascular blood pump is operating. For example, advantages may be realized by determining ventricular volume, such as while the intravascular pump or other device remains within the patient's heart. In some instances, the ventricular volume may be used to improve the functionality of the intravascular blood pump and other devices. The ventricular volume also may be used to assess cardiac performance and cardiac unloading.

According to embodiments described herein, the ventricular volume may be determined using a conductance or admittance method. Such real-time ventricular volume measurements may then be used to generate pressure-volume loops from which cardiac performance and the level of cardiac unloading may be evaluated. In some embodiments, ventricular volume may be assessed without the need to insert a dedicated conductance or admittance catheter.

In view of the above, the inventors have recognized the benefits of an electrode assembly patch (also referred to herein as "the patch") that is attached or attachable to an intravascular blood pump, such as to the cannula of such pump, for measuring ventricular volume. As will be appreciated, although shown and described as being attachable to an intravascular blood pump, such an electrode assembly patch may be attachable to other suitable medical devices in other embodiments, such as to a portion of a catheter device. As will be further appreciated, although shown and described for measuring ventricular volume, the electrode assembly patch may be configured to measure other suitable parameters. Alternatively, the electrode assembly patch may be configured for the ablation of tissue. For example, such an electrode assembly patch may be attached or attachable to a catheter ablation device.

As described herein, the electrode assembly patch may be configured to maintain proper alignment and separation of one or more electrodes on the electrode assembly patch. For example, in some embodiments, the electrode assembly patch may include one or more inner electrodes measuring voltage and one or more outer electrodes configured to induce a current (with one of the electrodes being used as a ground). In such embodiments, the electrode assembly patch may allow a distance between the inner electrodes to be maintained fixed relative to one another and maintained at a prescribed distance, which may be as large as possible. In some embodiments, the electrode assembly patch also may allow the distances between an inner and outer electrode to be fixed relative to one another. In some embodiments, the electrode assembly patch may allow the electrodes to be arranged in a serial arrangement. The electrode assembly patch also may be configured to not encircle the entire circumference of the device (e.g., not include a ring shape) when applied to the device.

In some embodiments, the electrode assembly patch includes a flexible construction. For example, as disclosed herein, the electrode assembly patch may be wrapped, folded, wound (e.g. helically) or otherwise placed around an exterior of the device (e.g., cannula) to install the electrode assembly patch onto the device. In such embodiments, the electrode assembly patch may include a two-dimensional configuration when in an undeployed state and a three-dimensional configuration while in a deployed state.

In some embodiments, the electrode assembly patch may include a multi-layered construction. In such embodiments, the electrode assembly patch may allow the wirings to be totally encased and routed via the multi-layered construction to a desired location on the device (e.g., to an outflow cage). In such embodiments, at least a portion of the electrodes also may be exposed. In some embodiments, the electrode assembly patch also may include a non-conductive layer.

In some embodiments, the electrode assembly patch is configured to be low-profile such that there will be little or no change to the outer diameter of the device (e.g., cannula) after attachment of the electrode assembly patch. In such embodiments, the low-profile configuration may result in little to no change to the device's overall profile and functionality.

In some embodiments, the electrode assembly patch may be configured for easy application to the device (e.g., to the cannula). For example, as described herein, the electrode assembly patch may be thermoformed, glued, bonded, or otherwise suitably attached to the outer surface of the device (e.g., to the cannula).

In some embodiments, the electrode assembly patch may include one or more tabs to enable a proper application of the electrode assembly patch on the device and proper spacing between the electrodes. In some embodiments, the tabs also may provide mechanical stability to the electrode assembly patch while the electrode assembly patch is attached to the device.

FIG. 1 depicts an exemplary intravascular blood pump 100 adapted for left heart support, in accordance with aspects of the disclosure. In that regard, the intravascular blood pump 100 includes an elongate catheter 102, a motor 104, a cannula 110, a blood inflow cage 114 arranged at or near the distal end 112 of the cannula 110, a blood outflow cage 106 arranged at or near the proximal end 108 of the cannula 110, and an optional atraumatic extension 116 arranged at the distal end of the blood inflow cage 114.

Motor 104 is configured to rotatably drive an impeller (not shown), thereby generating suction sufficient to draw blood into cannula 110 through the blood inflow cage 114, and to expel the blood out of cannula 110 through the blood outflow cage 106. In that regard, the impeller may be positioned distal of the blood outflow cage 106, for example, within the proximal end 108 of the cannula 110 or within a pump housing 107 coupled to the proximal end 108 of the cannula 110. In some aspects of the technology, rather than the impeller being driven by an on-board motor 104, the impeller may instead be coupled to an elongate drive shaft which is driven by a motor located external to the patient.

Catheter 102 may house electrical lines coupling the motor 104 to one or more electrical controllers or other sensors. Alternatively, where the impeller is driven by an external motor, an elongate drive shaft may pass through catheter 102. Catheter 102 may also serve as a conduit for one or more wires (e.g., wire 502 of FIG. 5, described below) connecting the electrodes described herein to one or more controllers, power sources, etc. (e.g., as included in controller 302 of FIG. 3, described below) located outside the patient's body. Catheter 102 may also include a purge fluid conduit, a lumen configured to receive a guidewire, etc.

The blood inflow cage 114 includes one or more apertures or openings configured to allow blood to be drawn into cannula 110 when the motor 104 is operating. Likewise, blood outflow cage 106 includes one or more apertures or openings configured to allow blood to flow from the cannula 110 out of the intravascular blood pump 100. Blood inflow cage 114 and outflow cage 106 may be composed of any suitable bio-compatible material(s). For example, blood inflow cage 114 and/or blood outflow cage 106 may be formed out of bio-compatible metals such as stainless steel, titanium, or biocompatible polymers such as polyurethane. In addition, the surfaces of blood inflow cage 114 and/or blood outflow cage 106 may be treated in various ways, including, but not limited to etching, texturing, or coating or plating with another material. For example, the surfaces of blood inflow cage 114 and/or blood outflow cage 106 may be laser textured.

Cannula 110 may include a flexible hose portion. For example, cannula 110 may be composed, at least in part, of a polyurethane material. In addition, cannula 110 may include a shape-memory material. For example, cannula 110 may comprise a combination of a polyurethane material and one or more strands or coils of a shape-memory material such as Nitinol. Cannula 110 may be formed such that it includes one or more bends or curves in its relaxed state, or it may be configured to be straight in its relaxed state. In that regard, in the exemplary arrangement shown in FIG. 1, the cannula 110 has a single pre-formed anatomical bend 118 based on the portion of the left heart in which it is intended to operate. Despite this bend 118, the cannula 110 may nevertheless also be flexible, and may thus be capable of straightening (e.g., during insertion over a guidewire), or bending further (e.g., in a patient whose anatomy has tighter dimensions). Further in that regard, cannula 110 may include a shape-memory material configured to allow the cannula 110 to be a different shape (e.g., straight or mostly straight) at room temperatures, and to form bend 118 once the shape-memory material is exposed to the heat of a patient's body.

Atraumatic extension 116 may assist with stabilizing and positioning the intravascular blood pump 100 in the correct position in the patient's heart. Atraumatic extension 116 may be solid or tubular. If tubular, atraumatic extension 116 may be configured to allow a guidewire to be passed through it to further assist in the positioning of the intravascular blood pump 100. Atraumatic extension 116 may be any suitable size. For example, atraumatic extension 116 may have an outer diameter in the range of 4-8 Fr. Atraumatic extension 116 may be composed, at least in part, of a flexible material, and may be any suitable shape or configuration such as a straight configuration, a partially curved configuration, a pigtail-shaped configuration as shown in the example of FIG. 1, etc. Atraumatic extension 116 may also have sections with different stiffnesses. For example, atraumatic extension 116 may include a proximal section that is stiff enough to prevent it from buckling, thereby keeping the blood inflow cage 114 in the desired location, and a distal section that is softer and has a lower stiffness, thereby providing an atraumatic tip for contact with a wall of the patient's heart and to allow for guidewire loading. In such a case, the proximal and distal sections of the atraumatic extension 116 may be composed of different materials, or may be composed of the same material, treated to provide different stiffnesses.

Notwithstanding the foregoing, as mentioned above, atraumatic extension 116 is an optional structure. In that regard, the present technology may also be used with intravascular blood pumps and other intracardiac devices that include extensions of different types, shapes, materials, and qualities. Likewise, the present technology may be used with intravascular blood pumps and other intracardiac devices that have no distal extensions of any kind.

Intravascular blood pump 100 may be inserted percutaneously. For example, when used for left heart support, intravascular blood pump 100 may be inserted via a catheterization procedure through the femoral artery or axillary artery, into the aorta, across the aortic valve, and into the left ventricle. Once positioned in this way, the intravascular blood pump 100 may deliver blood from the blood inflow cage 114, which may sit inside the left ventricle, through cannula 110, to the blood outflow cage 106, which may sit inside the ascending aorta. In some aspects of the technology, intravascular blood pump 100 may be configured such that bend 118 will rest against a predetermined portion of the patient's heart when the intravascular blood pump 100 is in a desired location. Likewise, the atraumatic extension 116 may be configured such that it rests against a different predetermined portion of the patient's heart when the intravascular blood pump 100 is in the desired location.

Figure 2:
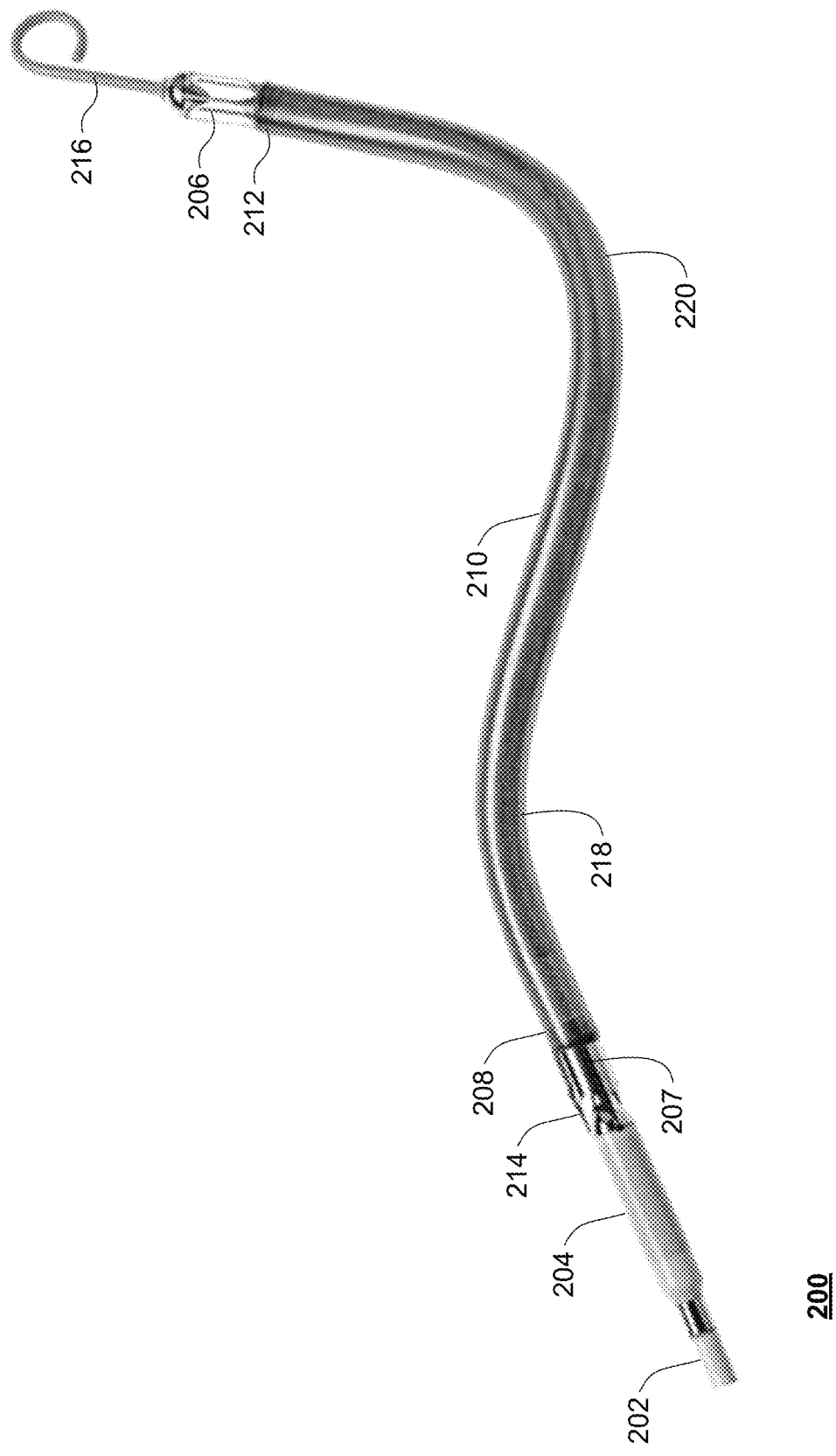
FIG. 2 depicts a schematic perspective view of an exemplary intravascular blood pump configured for right heart support, in accordance with aspects of the disclosure.

FIG. 2 depicts an exemplary intravascular blood pump 200 adapted for right heart support, in accordance with aspects of the disclosure. In that regard, the intravascular blood pump 200 includes an elongate catheter 202, a motor 204, a cannula 210, a blood inflow cage 214 arranged at or near the proximal end 208 of the cannula 210, a blood outflow cage 206 arranged at or near the distal end 212 of the cannula 210, and an optional atraumatic extension 216 arranged at the distal end of the blood outflow cage 206.

As with the exemplary blood pump of FIG. 1, motor 204 is configured to rotatably drive an impeller (not shown), thereby generating suction sufficient to draw blood into cannula 210 through the blood inflow cage 214, and to expel the blood out of cannula 210 through the blood outflow cage 206. In that regard, the impeller may be positioned distal of the blood inflow cage 214, for example, within the proximal end 208 of the cannula 210 or within a pump housing 207 coupled to the proximal end 208 of the cannula 210. Here as well, in some aspects of the technology, rather than the impeller being driven by an in-dwelling motor 204, the impeller may instead be coupled to an elongate drive shaft which is driven by a motor located external to the patient.

The cannula 210 of FIG. 2 may serve the same purpose, and may have the same properties and features described above with respect to cannula 110 of FIG. 1. However, in the exemplary arrangement shown in FIG. 2, the cannula 210 has two pre-formed anatomical bends 218 and 220 based on the portion of the right heart in which it is intended to operate. Here again, despite the existence of bends 218 and 220, the cannula 210 may nevertheless also be flexible, and may thus be capable of straightening (e.g., during insertion over a guidewire), or bending further (e.g., in a patient whose anatomy has tighter dimensions). Further in that regard, cannula 210 may include a shape-memory material configured to allow the cannula 210 to be a different shape (e.g., straight or mostly straight) at room temperatures, and to form bends 218 and/or 220 once the shape-memory material is exposed to the heat of a patient's body.

The catheter 202 and atraumatic extension 216 of FIG. 2 serve the same purpose and may have the same properties and features described above with respect to catheter 102 and atraumatic extension 116 of FIG. 1. Likewise, other than being located at opposite ends of the cannula from those of FIG. 1, the blood inflow cage 214 and blood outflow cage 206 of FIG. 2 are similar to the blood inflow cage 114 and blood outflow cage 106 of FIG. 1, and thus may have the same properties and features described above.

Like the exemplary blood pump of FIG. 1, the intravascular blood pump 200 of FIG. 2 may also be inserted percutaneously. For example, when used for right heart support, intravascular blood pump 200 may be inserted via a catheterization procedure through the femoral vein, into the inferior vena cava, through the right atrium, across the tricuspid valve, into the right ventricle, through the pulmonary valve, and into the pulmonary artery. Once positioned in this way, the intravascular blood pump 200 may deliver blood from the blood inflow cage 214, which may sit inside the inferior vena cava, through cannula 210, to the blood outflow cage 206, which may sit inside the pulmonary artery.

Figure 3:
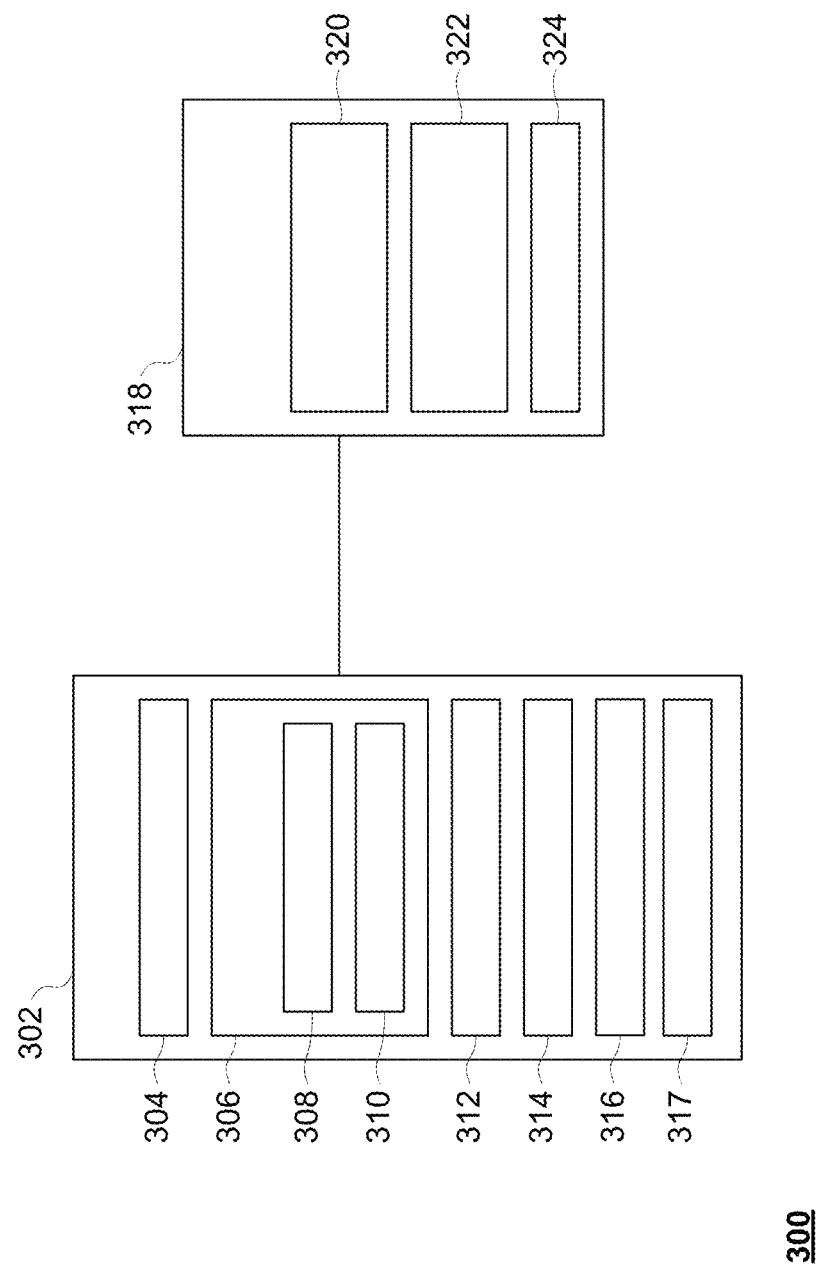
FIG. 3 is a functional block diagram of an exemplary system, in accordance with aspects of the disclosure.

As described herein, the intravascular pump may be configured to assess ventricular volume (and thus cardiac performance and cardiac unloading) while the intravascular blood pump or other device remains within the patient's heart via one or more electrodes that induce current and one or more electrodes that measure voltage. FIG. 3 is a functional block diagram of an exemplary system, in accordance with aspects of this disclosure. In the example of FIG. 3, the system 300 includes an intravascular blood pump 318 and a controller 302. The intravascular blood pump 318 may take any form, including those shown in the exemplary intravascular blood pumps 100 and 200 of FIG. 1 or 2, respectively.

As shown in the example of FIG. 3, the intravascular blood pump 318 of FIG. 3 may include one or more pressure sensors 322 and a motor 324. The intravascular blood pump 318 may include an attached electrode assembly patch 320 such as the electrode assembly patches 400, 600, 700, 800 shown in FIGS. 4A, 4B, 6A, 6B, 7A, 7B, and 8.

As described herein, the electrode assembly patch 320 may include one or more electrodes. For example, as shown in FIG. 4D, the electrode assembly patch 400 may include at least two electrodes configured to provide (e.g., induce) a current (e.g., electrodes 454a and 454d of FIG. 4D, the electrodes of electrode tabs 606a and 606d of FIG. 6, the electrodes of electrode tabs 706a and 706d of FIG. 7, and the electrodes 806a and 806d of FIG. 8, as described further below), and at least two electrodes configured to measure voltage (e.g., electrodes 454b and 454c of FIG. 4D, the electrodes of electrode tabs 606b and 606c of FIG. 6, the electrodes of electrode tabs 706b and 706c of FIG. 7, and the electrodes 806b and 806c of FIG. 8, as described further below).

In some embodiments, one or more pressure sensors 322 may include any suitable type of pressure sensor or combination of pressure sensors configured to measure pressure at or near the electrodes of the electrode assembly patch 320. Thus, in some aspects of the technology, the pressure sensor(s) 322 may be a single pressure sensor positioned at or near the distal end of the cannula (e.g., cannula 110 or 210). Likewise, in some aspects of the technology, the pressure sensor(s) 322 may be a combination of a pressure sensors whose readings may be combined to derive an estimated pressure in the vicinity of the set of electrodes of the electrode assembly patch 320.

In the example of FIG. 3, the controller 302 may include one or more processors 304 coupled to memory 306 storing instructions 308 and data 310, a device interface 312 with the intravascular blood pump 318, a current source 314, a power source 316, and a voltage measurement unit 317. The device interface 312 may be any suitable type of interface between controller 302 and intravascular blood pump 318 that is capable of providing current from current source 314 to the electrodes of the electrode assembly patch 320, receiving voltage readings from the electrodes of the electrode assembly patch 320, receiving pressure readings from pressure sensor(s) 322, and providing power from power supply 316 to motor 324. Current source 314 may be any device capable of providing a suitable current for performing conductance or admittance measurements. For example, current source 314 may be configured to provide a substantially constant alternating current of 10 and 100 µA at 20 kHz. As will be understood, in some aspects of the technology, current source 314 and power supply 316 may be implemented as a single unit configured to both power the motor 324 and provide a suitable current to the electrodes of the electrode assembly patch 320.

Controller 302 may take any form. In that regard, controller 302 may comprise a single modular unit, or its components may be distributed between two or more physical units. Controller 302 may further include any other components normally used in connection with a computing device such as a user interface. In that regard, controller 302 may have a user interface that includes one or more user inputs (e.g., buttons, touchscreen, keypad, keyboard, mouse, microphone, etc.); one or more electronic displays (e.g., a monitor having a screen or any other electrical device that is operable to display information, one or more lights, etc.); one or more speakers, chimes or other audio output devices; and/or one or more other output devices such as vibrating, pulsing, or haptic elements.

The one or more processors 304 and memory 306 described herein may be implemented on any type of computing device(s), including customized hardware or any type of general computing device. Memory 306 may be of any non-transitory type capable of storing information accessible by the processor(s) 304, such as a hard-drive, memory card, optical disk, solid-state drive, tape memory, or similar structure.

Instructions 308 may include programming configured to receive and process readings from the set of electrodes 320 and the one or more pressure sensors 322. In that regard, instructions 308 may include the programming necessary to calculate voltage drops and/or phase shift (e.g., using voltage measurement unit 317) between the voltage-reading electrodes of the electrodes of the electrode assembly patch 320 (e.g., electrodes 454b and 454c of FIG. 4D, the electrodes of electrode tabs 606b and 606c of FIG. 6, the electrodes of electrode tabs 706b and 706c of FIG. 7, and the electrodes 806b and 806c of FIG. 8, as described further below), calculate conductance or admittance based on the readings received from the electrodes of the electrode assembly patch 320 and the one or more pressure sensors 322, estimate ventricular volume based on conductance or admittance calculations, generate pressure-volume loops based on estimated ventricular volume, generate estimates of cardiac performance based on generated pressure-volume loops, and/or generate estimates of ventricular unloading provided by the operation of the intravascular blood pump 318 based on generated pressure-volume loops. Controller 302 may further be configured to store readings from the set of electrodes 320 and the one or more pressure sensors 322, and calculations based thereon, in memory 306. In some embodiments, the controller 302 also may be configured to send readings from the electrodes of the electrode assembly patch 320 and/or generated estimates of ventricular unloading or cardiac performance to an external device, such as to a user interface (not shown) and/or to a cloud-based storage devices where the readings and/or generated estimates may be stored.

Data 310 may include any relevant data for operating the intravascular blood pump 318. For example, data 310 may include lookup tables and other data relevant to interpreting signals from the intravascular blood pump 318, calibrating and/or interpreting the signals of the electrodes of the electrode assembly patch 320 or the one or more pressure sensors 322, etc.

Figure 4A:
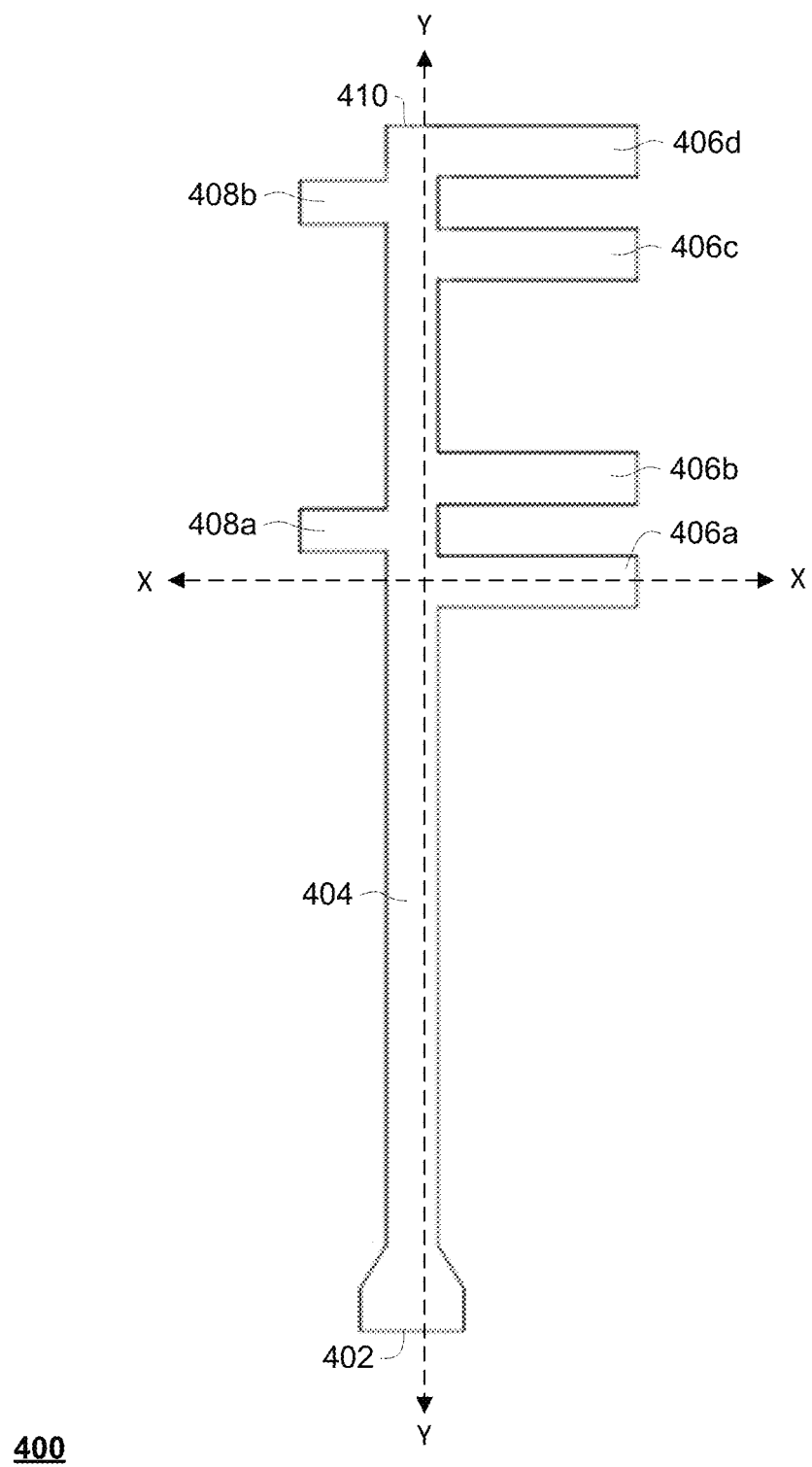
FIG. 4A depicts a schematic top view of an exemplary electrode assembly patch, in accordance with aspects of the disclosure.

FIG. 4A depicts an exemplary electrode assembly patch 400, in accordance with aspects of the disclosure. As shown in FIG. 4D, the exemplary electrode assembly patch 400 is configured as a multi-layered strip 404, extending longitudinally (e.g., in the direction of line Y-Y) from a proximal end 402 to a distal end 410.

Figure 4B:
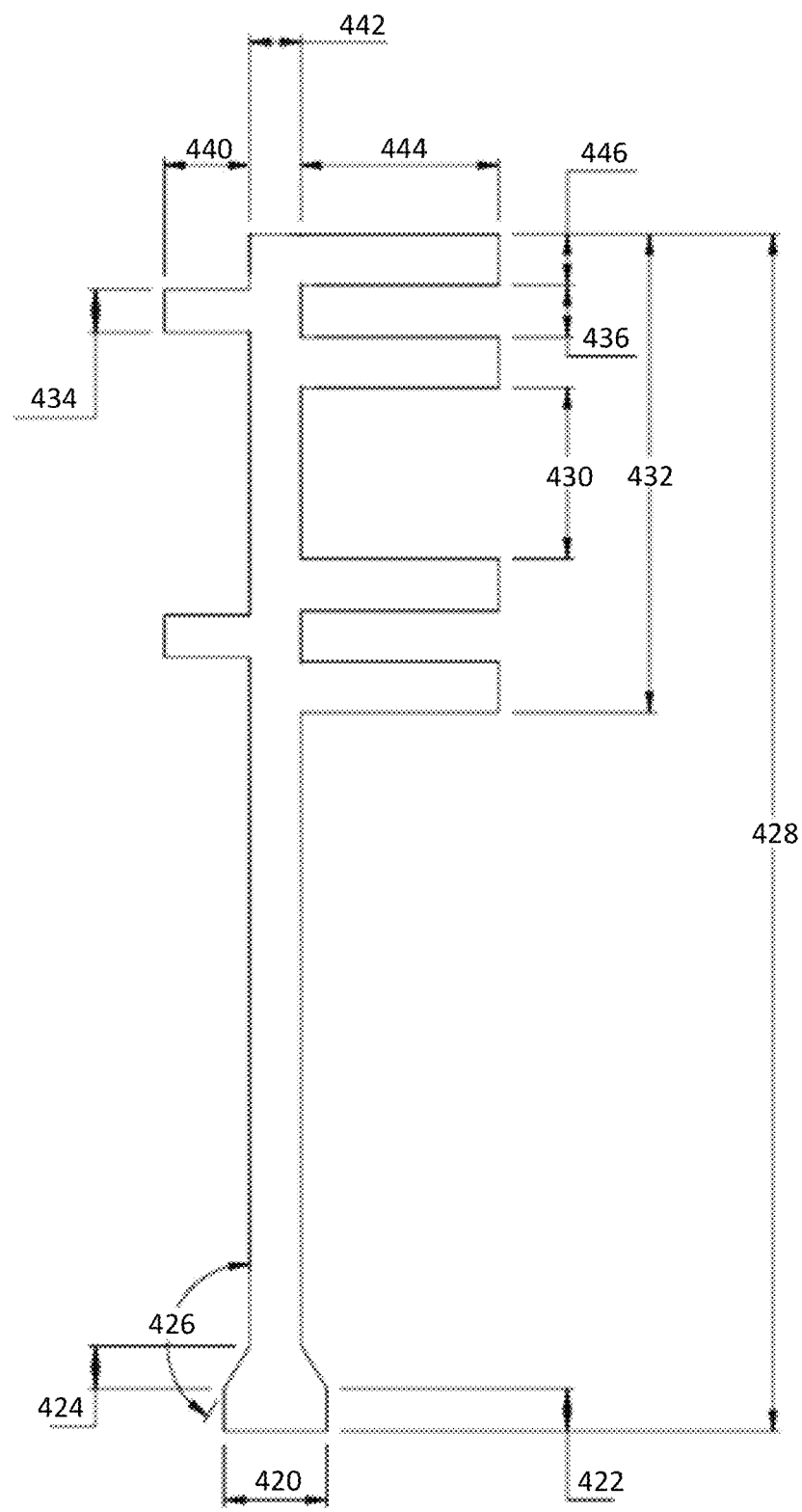
FIG. 4B depicts selected dimensions of the electrode assembly patch of FIG. 4A, in accordance with aspects of the disclosure.

In some embodiments, as shown in FIGS. 4A and 4B, the electrode assembly patch 400 may include one or more tabs extending outwardly and away from the strip. For example, one or more tabs may extend outwardly and away from a first side of the strip in a first direction and one or more tabs may extend outwardly and away from a second, opposite side of the strip in a second, opposite direction. In some embodiments, the tabs may extend to the left and right of the strip.

As shown in FIGS. 4A and 4B, in some embodiments, the tabs may be perpendicular to the strip. In other embodiments, one or more tabs may extend at other suitable angles relative to the strip. For example, the tabs may extend ±45 degrees relative to the latitudinal axis of the strip. In some embodiments, as shown in FIGS. 4A and 4B, the tabs may be positioned parallel to one another. As will be appreciated, in other embodiments, one or more tabs may extend in a direction non-parallel to another tab (or tabs as the case may be).

As shown in FIG. 4A, the tabs labeled 406a, 406b, 406c, and 406d and extending to the right of the strip 404 are electrode tabs. For purposes herein electrode tabs include tabs in which an electrode extends at least partially therein. As described herein, the electrodes may induce a current in some embodiments and/or measure voltage in other embodiments. In some embodiments, the tabs labeled 408a and 408b and extending to the left of the strip are non-conductive stabilizer tabs. In some embodiments, the non-conductive stabilizer tabs may be used both to ensure separation and proper alignment of the electrode tabs (when wrapped around an intravascular device), and to enhance adhesion and stabilize the electrode assembly patch when it is being affixed to a portion of an intravascular blood pump or other device (e.g., using thermoforming, bonding, gluing, etc.).

Figure 4C:
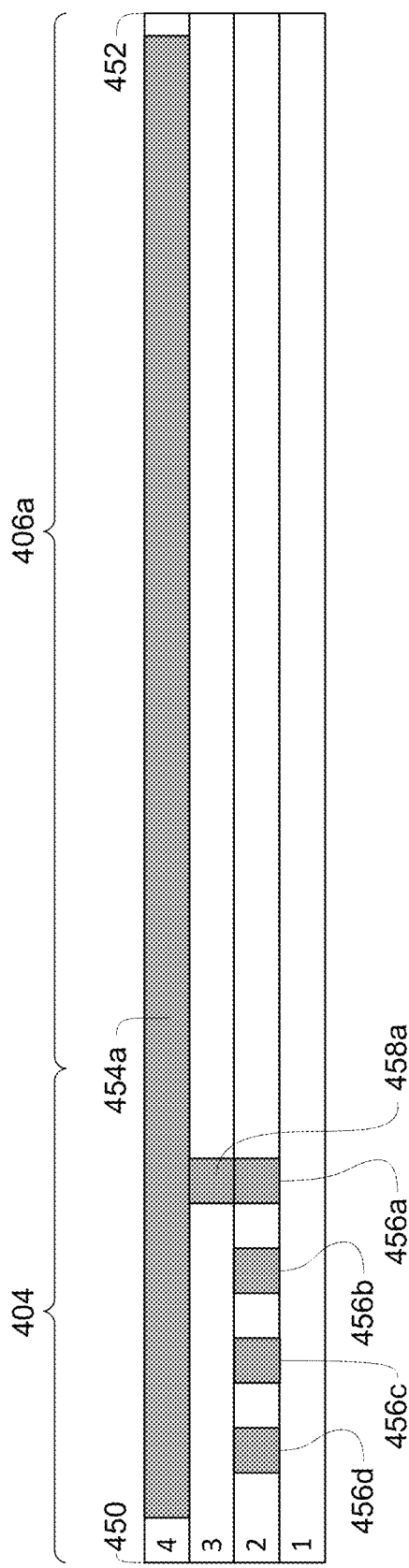
FIG. 4C depicts a schematic cross-sectional view of the electrode assembly patch of FIG. 4A taken along line X-X, in accordance with aspects of the disclosure.
Figure 4D:
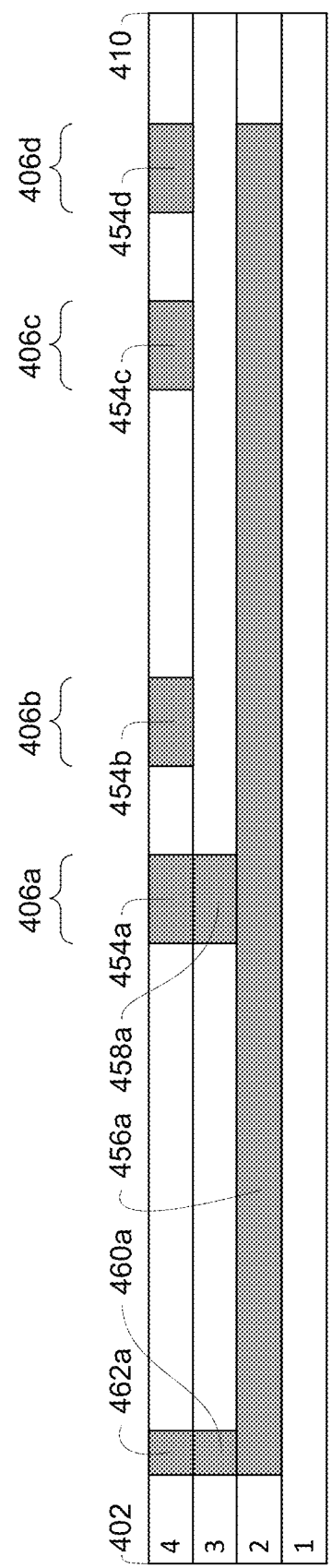
FIG. 4D depicts a schematic cross-sectional view of the electrode assembly patch of FIG. 4A taken along line Y-Y, in accordance with aspects of the disclosure.
Figure 4E:
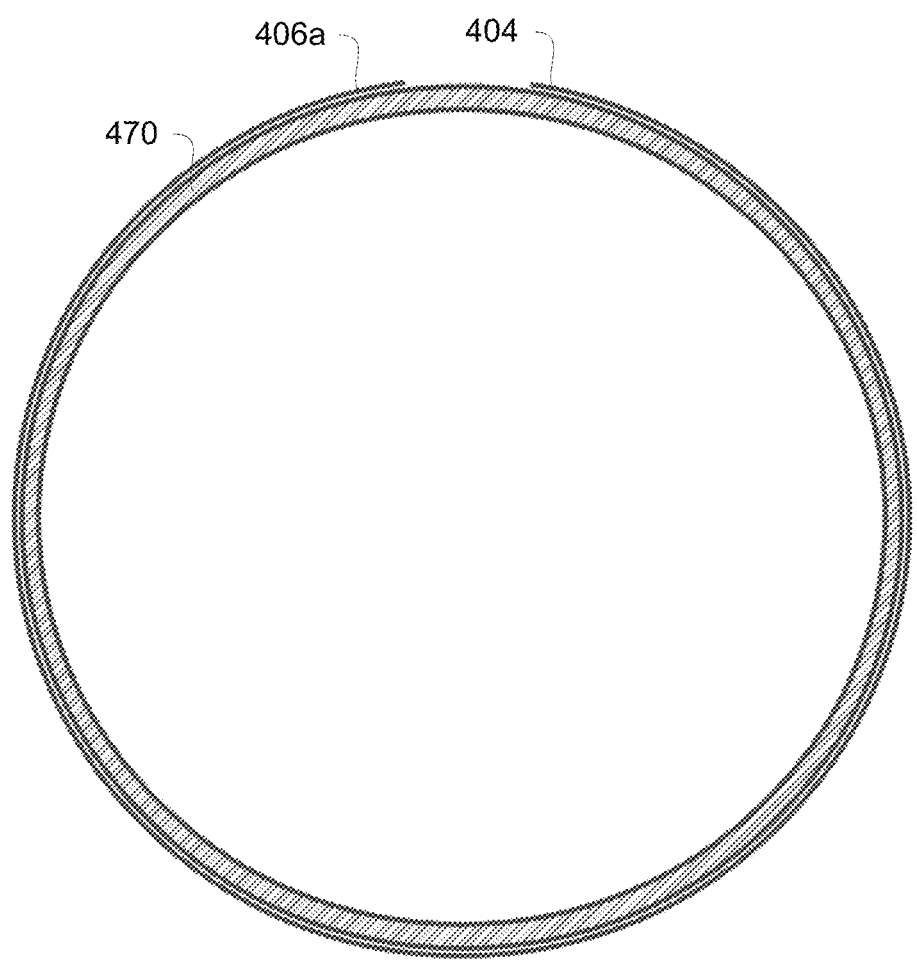
FIG. 4E depicts a schematic cross-sectional top view of the electrode assembly patch of FIG. 4A attached to a cannula of an intravascular pump.

In some embodiments, as shown in FIG. 4E, when attached to the intravascular device, the electrode tabs (e.g., electrode tab 406a of FIG. 4E) are configured to wrap around only a portion of an intravascular device 470. That is, in such embodiments, the electrode tabs do not encircle an entire circumference of the device. In other words, in such embodiments, the electrodes of the electrode assembly patch do not form closed rings when the electrode assembly patch is attached to the device (e.g., a distal end of the electrode tab is spaced from the adjacent portion of the strip).

Although the example of FIG. 4A depicts all of the electrode tabs extending to the right of strip 404, and all of the stabilizer tabs extending to the left of the strip 404, it will be understood that any suitable arrangement may be used. For example, in some aspects of the technology, the directions of each tab may be reversed from what is shown in FIG. 4A. Likewise, in some aspects of the technology, the tabs labeled 406a, 406b, and 408b may each extend to the left of strip 404, and the tabs labeled 408a, 406c, and 406d may each extend to the right of strip 404.

Although the example of FIG. 4A depicts an electrode assembly patch with both electrode tabs and stabilizer tabs, in other embodiments, the electrode assembly patch may include only electrode tabs. As will be appreciated, in such an example, the electrodes tabs may have any suitable arrangement relative to the strip.

As shown in FIG. 4A, the strip 404 may have a tapered section at or near its proximal end 402. In such embodiments, the strip 404 may be wider at or near the proximal end 402 than at the distal end 410 (or another suitable portion of the strip). In some embodiments, the wider portion at or near the proximal end 402 may be used for welding or bonding external wires (e.g., wires 504 of FIG. 5) to contacts located at or near the proximal end 402 (e.g., contacts 462a-462d of FIG. 5). In cases where one or more wires are welded to each contact, a further layer of non-conductive material may be applied over top of the welds to electrically insulate the exposed wires and/or the weld from ambient fluids.

Although the exemplary electrode assembly patch 400 of FIG. 4A is shown with four electrode tabs, in some aspects of the technology, it may be implemented with additional or fewer electrode tabs (e.g., such that the total number of electrode tabs is 2, 6, 8, 10, 12, etc.). In addition, although the exemplary electrode assembly patch 400 is shown in FIGS. 4C and 4D having four layers, any other number of layers and arrangement of conductors may be employed.

It will be understood that the exemplary electrode assembly patch 400 of FIG. 4A may be adapted to any suitable intravascular blood pump, and that its dimensions may be customized to whatever device it is applied to. In that regard, FIG. 4B depicts a copy of the exemplary electrode assembly patch 400 of FIG. 4A, annotated to show various features and dimensions that may be modified to adapt the assembly to different intravascular blood pumps or other devices. For purposes of illustration, each of the features and dimensions depicted in FIG. 4B will be described below using the assumption that the electrode assembly patch is to be applied (e.g., thermoformed, glued, bonded, etc.) to the outer surface of a cannula (e.g., cannula 110 of FIG. 1) of an intravascular blood pump. It is further assumed that the cannula has a length of at least 70 mm and a diameter of about 14 Fr (4.67 mm). Although FIGS. 4A and 4B depict the same exemplary electrode assembly patch 400, for clarity, the elements identified in FIG. 4A have not been identified again in FIG. 4B.

Using the assumptions set forth above, the electrode assembly patch 400 of FIG. 4B may have a total length 428 of 70 mm. The proximal end 402 of the strip 404 may have a contact patch with a width 420 of 6 mm and length 422 of 2.5 mm, which then tapers down to a width 442 of 3 mm. The tapered section may have a length 424 of 2.5 mm, and a taper angle 426 of approximately 149°.

The four electrode tabs may each have a width 446 of 3 mm, and may be arranged such that the first and second tabs (406a and 406b of FIG. 4A) and the third and fourth tabs (406c and 406d of FIG. 4A) are spaced apart by a distance 436 of 3 mm, and such that the second and third tabs (406b and 406c of FIG. 4A) are separated by a distance 430 of 10 mm. As such, the set of four electrode tabs may span a total length 432 of 28 mm. In some aspects of the technology, it may be desirable to maximize the distance 430 between the second and third tabs (406b and 406c of FIG. 4A). As such, where the dimensions of the intravascular blood pump and/or the patient's anatomy allows distance 430 to be increased, it may be advantageous to do so, provided that all four electrode tabs may still fit within the volume to be measured (e.g., a patient's left ventricle).

The length 444 of each electrode tab may be configured such that the end of each tab will approach, but not overlap, the left edge of the strip when the tab is wrapped around the outside of the cannula. In that regard, given that a cannula with a diameter of 14 Fr will have a circumference of approximately 14.66 mm, and given that the strip has a width 442 of 3 mm, each electrode tab may have a length 444 of 11.5 mm, such that a gap of approximately 0.16 mm remains when the tab is wrapped around the cannula. It will be understood that avoiding overlap is not essential to the present technology, but may provide advantages in certain cases. For example, if the electrode assembly patch 400 is thermoformed to a portion of an intravascular blood pump, an overlap may cause the end of the electrode tab to melt together with a portion of the strip, which may cause a short to form between an electrode (e.g., electrode 454a of FIG. 4C) and one of the conductors for another electrode (e.g., wires 456b, 456c, or 456d of FIG. 4C). Likewise, as the material of electrode assembly patch 400 may not adhere to itself as strongly as it adheres to the cannula (or whatever other portion of the intravascular blood pump it may be applied to), an overlap may create an area of weakness where the tab may begin to peel up and delaminate. Further, avoiding overlap may be desirable for minimizing the overall diameter of the intravascular blood pump and/or to achieve a smoother outer profile when the electrode assembly patch 400 is applied to the surface of the intravascular blood pump.

In the example of FIGS. 4A and 4B, the first stabilizer tab (408a of FIG. 4A) is positioned such that it may fit between the distal ends of the first and second electrode tabs (406a and 406b of FIG. 4A) when the electrode assembly patch 400 is wrapped around the intravascular blood pump, and the second stabilizer tab (408b of FIG. 4A) is positioned such that it may fit between the distal ends of the third and fourth electrode tabs (406c and 406d of FIG. 4A). Thus, in the present example, the length 440 of each stabilizer tab may be 5 mm and the width 434 may be 2.5 mm. Using a width 434 of 2.5 mm allows for 0.25 mm of space to remain between the edges of each stabilizer tab and its two neighboring electrode tabs. Here as well, leaving a space between the edges of the stabilizer tab and its neighboring electrode tabs may be advantageous for ensuring that no overlaps are created during manufacturing that may adversely impact the overall diameter and/or smoothness of the outer profile, create weak points in the bond between the electrode assembly patch 400 and the cannula, etc.

Although each of the electrode tabs are showing as having the same width and length in FIG. 4A, it will be appreciated that the width and/or length of the tabs may vary from tab to tab (or between subsets of tabs). Similarly, although each of the stabilizer tabs are showing as having the same width and length in FIG. 4A, it will be appreciated that the width and/or length of the tabs may vary from tab to tab. Also, although each of the electrode and each of the stabilizer tabs are shown as having a uniform width, in other embodiments, one or more tabs may a width that varies between the proximal and distal ends (see e.g., the electrode tabs in FIG. 6A). For purposes herein, the proximal end of a tab is the end of the tab closest to the strip.

FIGS. 4C and 4D depict exemplary cross-sectional views of the electrode assembly patch of FIG. 4A, in accordance with aspects of the disclosure. More specifically, FIG. 4C depicts an exemplary cross-sectional view of the electrode assembly patch of FIG. 4A taken along line X-X, and thus shows a lateral cross-section spanning from a left edge 450 of strip 404 to a right edge 452 of electrode tab 406a. FIG. 4D depicts an exemplary cross-sectional view of the electrode assembly patch of FIG. 4A taken along line Y-Y, and thus shows a longitudinal cross-section spanning from the proximal end 402 to the distal end 410 of the electrode assembly patch of FIG. 4A.

As shown in the example of FIG. 4C, the electrode assembly patch may include four sandwiched layers (labeled 1-4 in FIGS. 4C and 4D). Layer 1 may be a non-conductive (dielectric) layer configured to adhere to a particular portion of the intravascular blood pump (or other device), and to electrically insulate the second layer from whatever surface the electrode assembly patch is applied to. For example, where the electrode assembly patch is to be applied to a flexible cannula (e.g., cannula 110 of FIG. 1) of an intravascular blood pump (e.g., intravascular blood pump 100 of FIG. 1), layer 1 may be made from a polymer (e.g., a polyamide film) suitable for gluing, bonding, or thermoforming to the cannula.

Layer 2 may contain wires 456a-456d, each of which runs between a contact patch (e.g., contact patch 462a) near the proximal end 402 of the electrode assembly patch and a respective electrode (454a-454d). Wires 456a-456d may be formed from any suitable metal or other conductive material, such as platinum, gold, silver, copper, etc. As shown in FIG. 4C, each of the wires 456a-456d may be spaced apart and separated by a non-conductive material (all white portions of layers 1-4 represent non-conductive material). In addition, non-conductive material may be also be used to fill the space between wire 456d and the left edge 450 of strip 404, and between 456a and the right edge of strip 404, such that wires 456a and 456d will also remain insulated from ambient fluids.

In some aspects of the technology, one or more of the portions of non-conductive material in layer 2 may result from the insertion of non-conductive strips prior to fusing the layers of the electrode assembly patch together (e.g., using thermoforming). Likewise, in some aspects of the technology, where the layers of the electrode assembly patch are fused using thermoforming, one or more of the portions of non-conductive material in layer 2 may result from non-conductive material melting and flowing into layer 2 from one or more adjacent layers (e.g., layer 1 or 3) during thermoforming. Here as well, the non-conductive material may be a polymer (e.g., a polyamide) or other suitable non-conductive material, including any of the non-conductive materials used in other layers.

Layer 3 may be another non-conductive layer configured to electrically insulate the wires 456a-456d from layer 4, except where a conductive bridge is provided to connect a given one of wires (e.g., wire 456a) to its respective contact patch (e.g., contact patch 462a) or its respective electrode (e.g., electrode 454a). For example, as shown in FIGS. 4C and 4D, a conductive bridge 458a is provided in a portion of layer 3 near electrode tab 406a in order to electrically connect wire 456a to electrode 454a. Likewise, as shown in FIG. 4D, a conductive bridge 460a is provided in a portion of layer 3 near proximal end 402 to electrically connect wire 456a to contact patch 462a. Here as well, the conductive bridges (e.g. 458a, 460a) may be formed from any suitable metal or other conductive material, such as platinum, gold, silver, copper, etc.

As above, one or more of the portions of non-conductive material in layer 3 may result from the insertion of non-conductive strips prior to fusing the layers of the electrode assembly patch together (e.g., using thermoforming). Likewise, in some aspects of the technology, where the layers of the electrode assembly patch are fused using thermoforming, one or more of the portions of non-conductive material in layer 3 may result from non-conductive material melting and flowing into layer 3 from one or more adjacent layers (e.g., layer 2 or 4) during thermoforming. Here as well, the non-conductive material of layer 3 may be a polymer (e.g., a polyamide) or other suitable non-conductive material, including any of the non-conductive materials used in other layers.

Layer 4 may contain the electrodes 454a-454d, each of which may be arranged to coincide with a corresponding electrode tab (406a-406d). As shown in FIG. 4D, each of the electrodes 454a-454d may be spaced apart and separated by a non-conductive material. Likewise, FIG. 4C shows a small amount of non-conductive material between the left end of electrode 454a and the left edge 450 of strip 404, and another small amount of non-conductive material between the right end of electrode 454a and the right edge 452 of electrode tab 406a. However, in some aspects of the technology, the electrode 454a may run the entire length from the left edge 450 of strip 404 to the right edge 452 of electrode tab 406a.

The top surface of each electrode 454a-454d may be exposed such that it can be used to provide a current to an ambient fluid (e.g., the blood within a patient's left ventricle), or sense voltage from that ambient fluid. Here as well, any suitable metal or other conductive material may be used for electrodes 454a-454d, such as platinum, gold, silver, copper, etc. In addition, electrodes 454a-454d may include a combination of conductive materials. For example, in some aspects of the technology, the electrodes 454a-454d may be formed from gold, and then coated or plated with a thin (e.g., a 100 nm) top layer of platinum.

As above, one or more of the portions of non-conductive material in layer 4 may result from the insertion of non-conductive strips prior to fusing the layers of the electrode assembly patch together (e.g., using thermoforming). Likewise, in some aspects of the technology, where the layers of the electrode assembly patch are fused using thermoforming, one or more of the portions of non-conductive material in layer 4 may result from non-conductive material melting and flowing into layer 4 from an adjacent layer (e.g., layer 3) during thermoforming. Here as well, the non-conductive material of layer 4 may be a polymer (e.g., a polyamide) or other suitable non-conductive material, including any of the non-conductive materials used in other layers.

Each of layers 1-4 may be any suitable thickness. For example, in some aspects of the technology, each layer may have a thickness of 5 such that the electrode assembly patch may have a total thickness of 20 µm. Likewise, in some aspects of the technology, each layer may have a thickness between 1-10 However, while FIGS. 4C and 4D show layers of equal thickness, in some aspects of the technology, one or more of the layers may be of a different thickness than the others. Likewise, although the example of FIGS. 4C and 4D show layers which have a constant thickness, in some aspects of the technology, the thickness of a layer may vary from left to right or from proximal to distal. For example, in some aspects of the technology, layers 1 and 2 may be formed using a first pre-formed sheet having a conductive film bonded to a non-conductive (dielectric) base which is etched such that only selected patches of the conductive film remain, and layers 3 and 4 may similarly be formed from a second pre-formed sheet of similar composition. In such cases, if the two sheets are combined using thermoforming, the non-conductive material from layers 1 and 3 may flow into adjacent layers 2 and 4 to bond the two sheets together and seal against any conductive material that remains in layers 2 and 4, resulting in the thickness of the electrode assembly patch varying slightly in areas with and without conductive film.

In addition, the thickness and materials of layers 1-4 may be selected such that suitable material properties are obtained for a given application. For example, where the electrode assembly patch is to be affixed to a flexible section of an intravascular blood pump such as the cannula (e.g., cannula 110 of FIG. 1), relatively thin layers may be used (e.g., 5 µm) and relatively flexible materials may be used for the non-conductive portions (e.g., polyamides) such that the entire electrode assembly patch will be capable of flexing with the section of the intravascular blood pump to which it is affixed.

Figure 5:
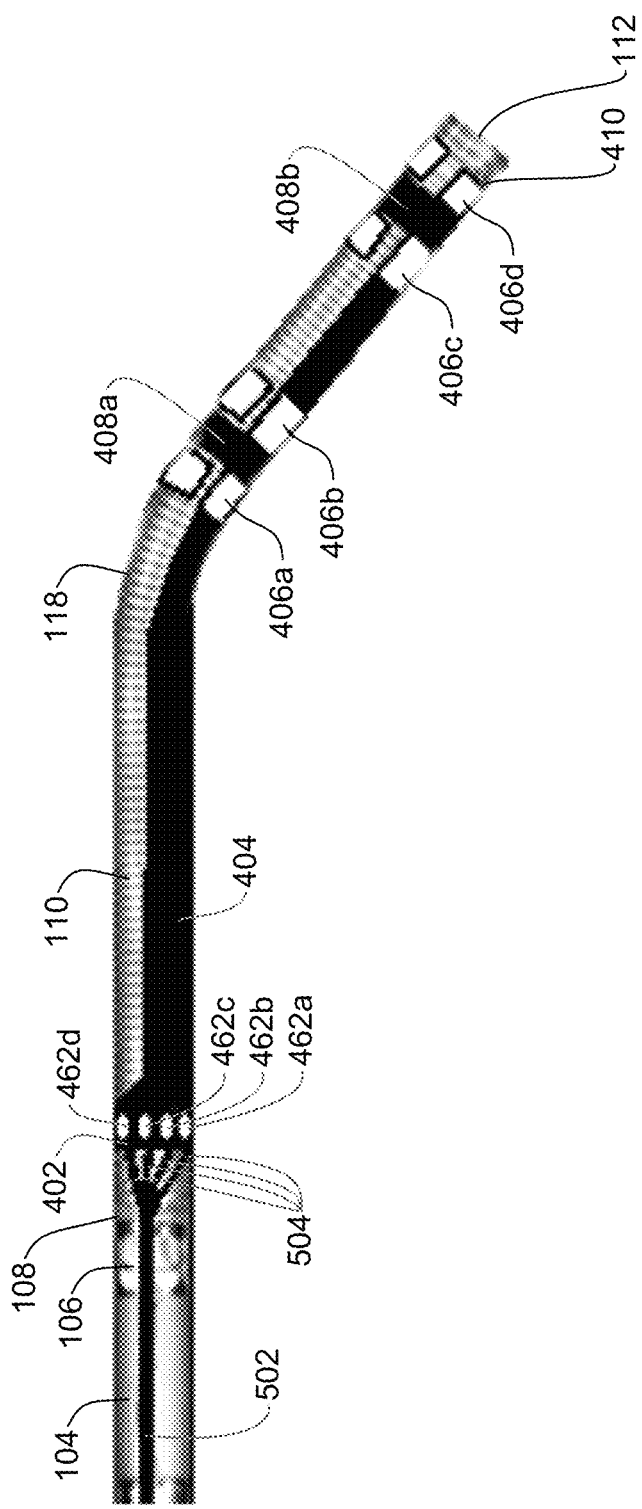
FIG. 5 depicts a schematic perspective view of an exemplary application of the electrode assembly patch of FIG. 4A to a portion of the exemplary intravascular blood pump of FIG. 1, in accordance with aspects of the disclosure.

FIG. 5 depicts an exemplary application of the electrode assembly patch of FIG. 4A to a portion of the exemplary blood pump of FIG. 1, in accordance with aspects of the disclosure. In that regard, FIG. 5 depicts a wire 502 routed along the outside of motor 104, along one of the struts of the blood outflow cage 106, where it fans out to individual wires 504, each of which connects to a different one of contact 462a-462d. In some aspects of the technology, wire 502 may travel within the elongate catheter 102 (not visible in FIG. 5), and may exit at a point near the proximal end of motor 104. As noted above, a coating or layer of non-conductive material may be applied over top of contact patches 462a-462d to insulate them from ambient fluids. Likewise, in some aspects of the technology, a coating or layer of non-conductive material may also be applied over top of wires 504. In some aspects of the technology, the non-conductive material may be a polymer sleeve (e.g., a polyamide sleeve) that is thermoformed over top of wires 504 and/or contact 462a-462d.

As will be appreciated, the electrode assembly patch may be joined to contacts located at other suitable locations of the intravascular pump. For example, in one embodiment, the electrode assembly patch may extend over at least a portion of the outflow cage 106 and extend into the catheter of the intravascular blood pump. In such an embodiment, the contacts and the electrode assembly patch may be placed inside the catheter of the intravascular blood pump for connection.

In the example of FIG. 5, the electrode assembly patch of FIG. 4A has been applied to the flexible cannula 110. As can be seen, the proximal end 402 of the strip 404 may be positioned near the proximal end 108 of the cannula 110, and the distal end 410 of the strip 404 may be positioned near the distal end 112 of the cannula 110. For example, in some embodiments, the distal end may be positioned near an inlet inflow cage (not shown) attached to the distal end of the cannula. In addition, each of the electrode tabs 406a-406d are arranged distal of the pre-formed anatomical bend 118 in cannula 110. In some aspects of the technology, the intravascular blood pump 100 may be configured such that the anatomical bend 118 will sit at or near the aortic valve. In such cases, arranging the electrode tabs 406a-406d distal of the pre-formed anatomical bend 118 may cause them to be positioned within a patient's left ventricle when the pump is in operation, such that they can be used to measure left ventricular volume.

In some aspects of the technology, the electrode assembly patch may be configured and/or applied such that the wires 456a-456d within strip 404 run along the side of the cannula (as opposed to running on the outside or the inside of anatomical bend 118). Although the electrode assembly patch may be formed to be thin and flexible (as described above), affixing it in this way may reduce stress on the wires 456a-456d which may lead to breakage, and/or may reduce the likelihood of the electrode assembly patch delaminating due to bending of the cannula 110.

The electrode assembly patch may be affixed to cannula 110 using any suitable method of bonding, gluing, thermoforming, etc. For example, in some aspects of the technology, the electrode assembly patch of FIGS. 4A-4D may be formed using one or more polyamides as the non-conductive material, gold as the conductive material (with or without a platinum plating on the top surface of electrodes 454a-454d), and may be thermoformed to the outer surface of cannula 110. In such a case, the electrode assembly patch may be laid over top of the cannula 110, covered with heat shrink tubing, and heated until the polyamide in layer 1 (and potentially some or all of the polyamide at the edges of other layers) fuses with the material of the cannula 110 (e.g., polyurethane).

Figure 6A:
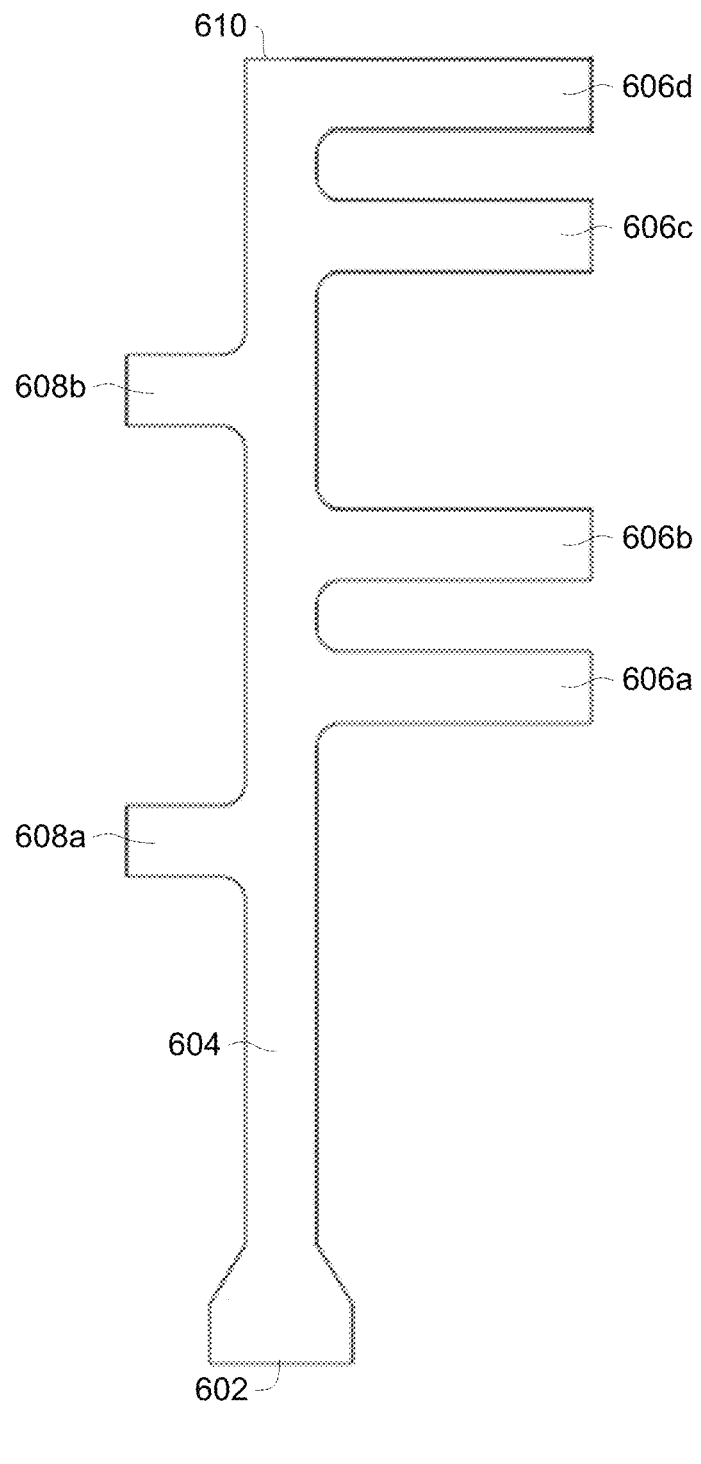
FIG. 6A depicts a schematic top view of an exemplary electrode assembly patch, in accordance with aspects of the disclosure.

FIG. 6A depicts another exemplary electrode assembly patch 600, in accordance with aspects of the disclosure. Here as well, the exemplary electrode assembly patch 600 may be configured as a multi-layered strip 604, which may have any suitable number and configuration of layers, including a configuration based on that which is discussed above with respect to FIGS. 4C and 4D. Like the example of FIG. 4A, strip 604 extends longitudinally from a proximal end 602 to a distal end 610, with a series of electrode tabs 606a, 606b, 606c, and 606d extending perpendicularly to the right, and two stabilizer tabs 608a and 608b extending to the left. In the example of FIG. 6A, the non-conductive stabilizer tabs are not positioned in between the electrode tabs when wrapped around the medical device. In that regard, the stabilizer tabs may function to stabilize the electrode assembly patch when it is being applied to a portion of an intravascular blood pump or other device (e.g., using thermoforming, bonding, gluing, etc.), and enhance adhesion, although not functioning as a separator tab. Similar to FIG. 4A, the strip 604 has a tapered section near its proximal end 602, which results in the strip 604 having a wider portion at proximal end 602 that may be used for welding or bonding external wires to contact located thereon.

Here as well, although the example of FIG. 6A depicts all of the electrode tabs extending to the right of strip 604, and all of the stabilizer tabs extending to the left of the strip 604, it will be understood that any suitable arrangement may be used. For example, in some aspects of the technology, the directions of each tab may be reversed from what is shown in FIG. 6A. Likewise, in some aspects of the technology, the tabs labeled 606a, 606b, and 608b may each extend to the left of strip 604, and the tabs labeled 608a, 606c, and 606d may each extend to the right of strip 404. Further, although the exemplary electrode assembly patch 600 of FIG. 6A is shown with four electrode tabs, in some aspects of the technology, it may be implemented with more or fewer additional sets of electrode tabs (e.g., such that the total number of electrode tabs is 2, 6, 8, 10, 12, etc.). Again, as with the above, although the electrode assembly patch is shown with two stabilizer tabs, it will be appreciated that the electrode assembly patch need not include stabilizer tabs, or may have more or fewer tabs. Also, the positions of the tabs along the longitudinal axis of the strip may vary in other embodiments.

Figure 6B:
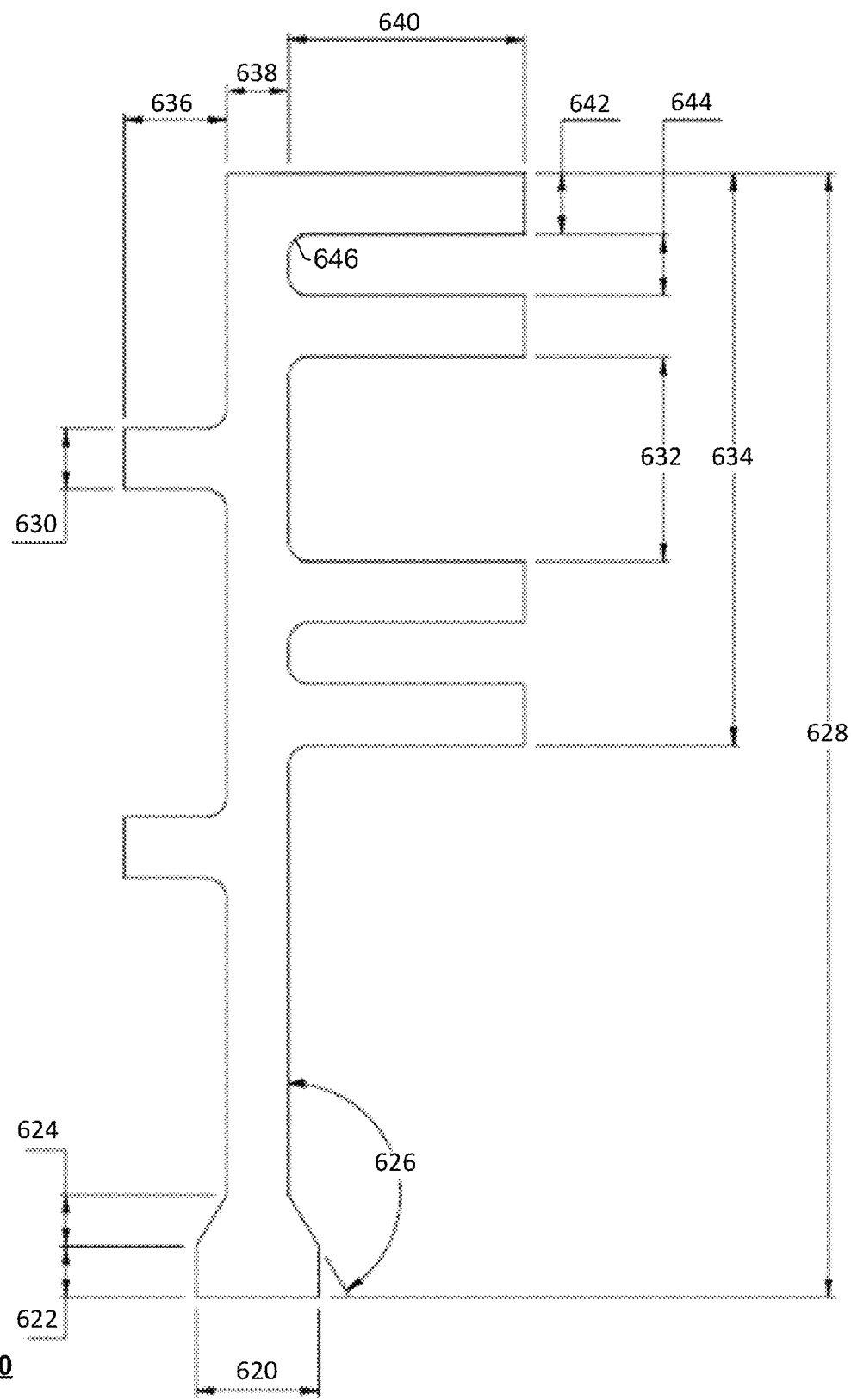
FIG. 6B depicts selected dimensions of the electrode assembly patch of FIG. 6A, in accordance with aspects of the disclosure.

It will be understood that the exemplary electrode assembly patch 600 of FIG. 6A may be adapted to any suitable intravascular blood pump, and that its dimensions may be customized to whatever device it is applied to. In that regard, FIG. 6B depicts a copy of the exemplary electrode assembly patch 600 of FIG. 6A, annotated to show various features and dimensions that may be modified to adapt the assembly to different intravascular blood pumps or other devices. For purposes of illustration, each of the features and dimensions depicted in FIG. 6B will be described below using the assumption that the electrode assembly patch is to be applied (e.g., thermoformed, glued, bonded, etc.) to the outer surface of a cannula (e.g., cannula 110 of FIG. 1) of an intravascular blood pump. It is further assumed that the cannula has a length of at least 55 mm and a diameter of about 14 Fr (4.67 mm). Although FIGS. 6A and 6B depict the same exemplary electrode assembly patch 600, for clarity, the elements identified in FIG. 6A have not be identified again in FIG. 6B.

Using the assumptions set forth above, the electrode assembly patch 600 of FIG. 6B may have a total length 628 of 55 mm. The proximal end of the strip may have a contact patch with a width 620 of 6 mm and length 622 of 2.5 mm, which then tapers down to a width 638 of 3 mm. The tapered section may have a length 624 of 2.5 mm, and a taper angle 626 of approximately 149°.

The four electrode tabs may each have a width 642 of 3 mm, and may be arranged such that the first and second tabs (606a and 606b of FIG. 6A) and the third and fourth tabs (606c and 606d of FIG. 6A) are spaced apart by a distance 644 of 3 mm, and such that the second and third tabs (606b and 606c of FIG. 6A) are separated by a distance 632 of 10 mm. As such, the set of four electrode tabs may span a total length 634 of 28 mm. Here as well, in some aspects of the technology, it may be desirable to maximize the distance 632 between the second and third tabs (606b and 606c of FIG. 6A). As such, where the dimensions of the pump and/or the patient's anatomy allows distance 632 to be increased, it may be advantageous to do so, provided that all four electrode tabs may still fit within the volume to be measured (e.g., a patient's left ventricle).

As in FIG. 4B, the length 640 of each electrode tab may be configured such that the end of each tab will approach, but not overlap, the left edge of the strip when the tab is wrapped around the outside of the cannula. In that regard, given that a cannula with a diameter of 14 Fr will have a circumference of approximately 14.66 mm, and given that the strip has a width 638 of 3 mm, each electrode tab may have a length 640 of 11.5 mm, such that a gap of approximately 0.16 mm remains when the tab is wrapped around the cannula. Here as well, it will be understood that avoiding overlap is not essential to the present technology, but may provide advantages in certain cases, as discussed above.

In the example of FIGS. 6A and 6B, the first stabilizer tab (608a of FIG. 6A) is positioned proximal of the first electrode tab (606a of FIG. 6A), and the second stabilizer tab (608b of FIG. 6A) is positioned between the second and third electrode tabs (606b and 606c of FIG. 6A) such that it may stabilize and reinforce adhesion of electrode assembly patch in the area between the second and third electrode tabs. As the stabilizer tabs of FIGS. 6A and 6B do not need to fit within the distance 644 between the first and second electrode tabs or between the third and fourth electrode tabs, they may have a broader range of dimensions than those of FIGS. 4A and 4B. In this example, it is assumed that each stabilizer tab has a length 636 of 5 mm and a width 630 of 3 mm.

As shown in FIGS. 6A and 6B, each of the stabilizer tabs 608a, 608b and each of the electrode tabs 606a-606d have curved sections (e.g., 646) where they join with strip 604. In some embodiments, rounding the corners in this way may reduce the chance that tearing and/or delamination of the electrode assembly patch may occur at these junctions. Any suitable profile may be used in these curved sections. For example, in some aspects of the technology, the curved sections may have a constant radius (e.g., 1 mm).

Figure 7A:
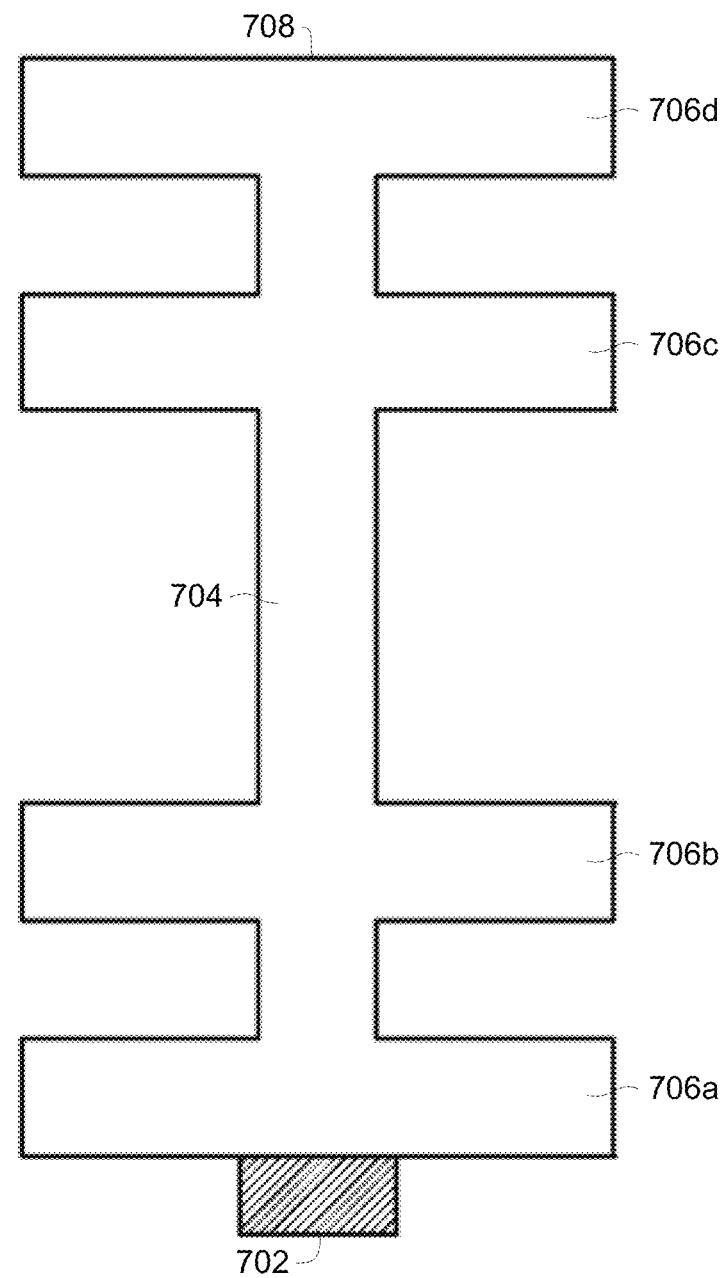
FIG. 7A depicts a schematic top view of an exemplary electrode assembly patch, in accordance with aspects of the disclosure.

FIG. 7A depicts a further exemplary electrode assembly patch 700, in accordance with aspects of the disclosure. Here as well, the exemplary electrode assembly patch 700 may be configured as a multi-layered strip 704, which may have any suitable number and configuration of layers, including a configuration based on that which is discussed above with respect to FIGS. 4C and 4D. In the example of FIG. 7A, strip 704 extends longitudinally from a proximal end 702 to a distal end 708, with a series of electrode tabs 706a, 706b, 706c, and 706d, each of which extends perpendicularly to strip 704 in both the left and the right direction. As with the above, in other embodiments, the tabs may extend at other suitable angles relative to the strip and to other tabs. As shown in the example of FIG. 7A, the strip 704 may be wider in the section at or near the proximal end of the strip (e.g., proximal the first electrode strip 706a), which may be helpful for welding or bonding external wires to contact patches located thereon.

Unlike the exemplary electrode assemblies 400 and 600 of FIGS. 4A and 6A, the wider portion of strip 704 at proximal end 702 directly abuts the first electrode strip 706a. This may result in the exemplary electrode assembly patch of 700 being shorter overall than the exemplary electrode assemblies 400 and 600 of FIGS. 4A and 6A, which may be advantageous in instances where the electrode assembly patch needs to be affixed to a shorter portion of an intravascular blood pump or other device, where wires to be connected to each contact patch are routed within a lumen or a wall of the cannula (e.g., cannula 110 of FIG. 1), etc. In contrast, the exemplary electrode assemblies 400 and 600 of FIGS. 4A and 6A may be advantageous where the electrode tabs (e.g., tabs 406*a*-406*d* of FIG. 4A, tabs 606*a*-606*d* of FIG. 6A) need to be positioned a longer distance from where the wires to be connected to each contact patch protrude from the catheter (e.g., catheter 102 of FIG. 1), as the portion of the strip (e.g., strip 404 of FIG. 4A, strip 604 of FIG. 6A) between the proximal end (e.g., proximal end 402 of FIG. 4A, proximal end 602 of FIG. 6A) and the first electrode tab (e.g., electrode tab 406*a* of FIG. 4A, electrode tab 606*a* of FIG. 6A) may be lower-profile, more flexible, more durable, and/or easier to affix to the cannula (e.g., cannula 110 of FIG. 1) than if a standard wire (e.g., wire 502) were to be affixed to the cannula.

Although the example of FIG. 7A depicts all of the electrode tabs extending both to the left and the right of strip 704, any suitable arrangement may be used. For example, in some aspects of the technology, all of the tabs may extend only to the right, or only to the left. Likewise, in some aspects of the technology, the tabs labeled 706*a* and 706*b* may each extend to the right of strip 704, and the tabs labeled 706*c* and 706*d* may each extend to the left of strip 704, or vice versa. Further, although the exemplary electrode assembly patch 700 of FIG. 7A is shown with four electrode tabs, in some aspects of the technology, it may be implemented with more or fewer sets of electrode tabs (e.g., such that the total number of electrode tabs is 2, 6, 8, 10, 12, etc.).

Figure 7B:
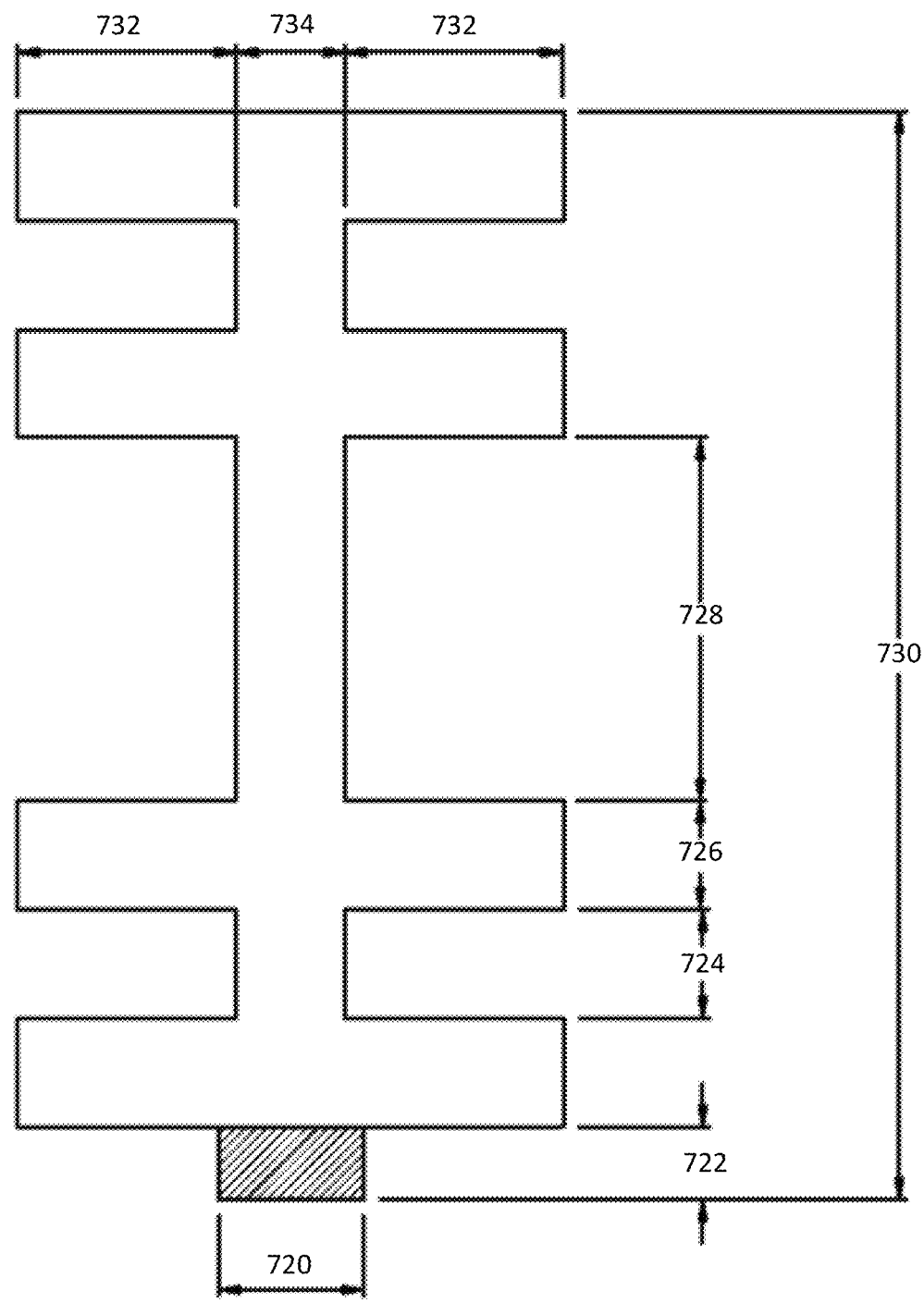
FIG. 7B depicts selected dimensions of the electrode assembly patch of FIG. 7A, in accordance with aspects of the disclosure.

It will be understood that the exemplary electrode assembly patch 700 of FIG. 7A may be adapted to any suitable intravascular blood pump, and that its dimensions may be customized to whatever device it is applied to. In that regard, FIG. 7B depicts a copy of the exemplary electrode assembly patch 700 of FIG. 7A, annotated to show various features and dimensions that may be modified to adapt the assembly to different intravascular blood pumps or other devices. For purposes of illustration, each of the features and dimensions depicted in FIG. 7B will be described below using the assumption that the electrode assembly patch is configured to be applied (e.g., thermoformed, glued, bonded, etc.) to the outer surface of a cannula (e.g., cannula 110 of FIG. 1) of an intravascular blood pump. It is further assumed that the cannula has a length of at least 30 mm and a diameter of about 14 Fr (4.67 mm). Although FIGS. 7A and 7B depict the same exemplary electrode assembly patch 700, for clarity, the elements identified in FIG. 7A have not been identified again in FIG. 7B.

Using the assumptions set forth above, the electrode assembly patch 700 of FIG. 7B may have a total length 730 of 30 mm. The proximal end of the strip may have a contact patch with a width 720 of 4 mm and length 722 of 2 mm.

The four electrode tabs may each have a width 726 of 3 mm, and may be arranged such that the first and second tabs (706*a* and 706*b* of FIG. 7A) and the third and fourth tabs (706*c* and 706*d* of FIG. 7A) are spaced apart by a distance 724 of 3 mm, and such that the second and third tabs (706*b* and 706*c* of FIG. 7A) are separated by a distance 728 of 10 mm. Here as well, in some aspects of the technology, it may be desirable to maximize the distance 728 between the second and third tabs (706*b* and 706*c* of FIG. 7A). As such, where the dimensions of the pump and/or the patient's anatomy allows distance 728 to be increased, it may be advantageous to do so, provided that all four electrode tabs may still fit within the volume to be measured (e.g., a patient's left ventricle).

Each electrode tab may extend to the right and the left of the strip by a distance 732 of 5.5 mm. Here as well, this distance 732 may be chosen such that the ends of each tab will approach each other, but not overlap. In that regard, given that a cannula with a diameter of 14 Fr will have a circumference of approximately 14.66 mm, and given that the strip has a width 734 of 3 mm, each electrode tab may extend to the right and to the left by a distance 732 of 5.5 mm, such that a gap of approximately 0.66 mm remains when the tab is wrapped around the cannula. Here as well, it will be understood that avoiding overlap is not essential to the present technology, but may provide advantages in certain cases, as discussed above.

Figure 8:
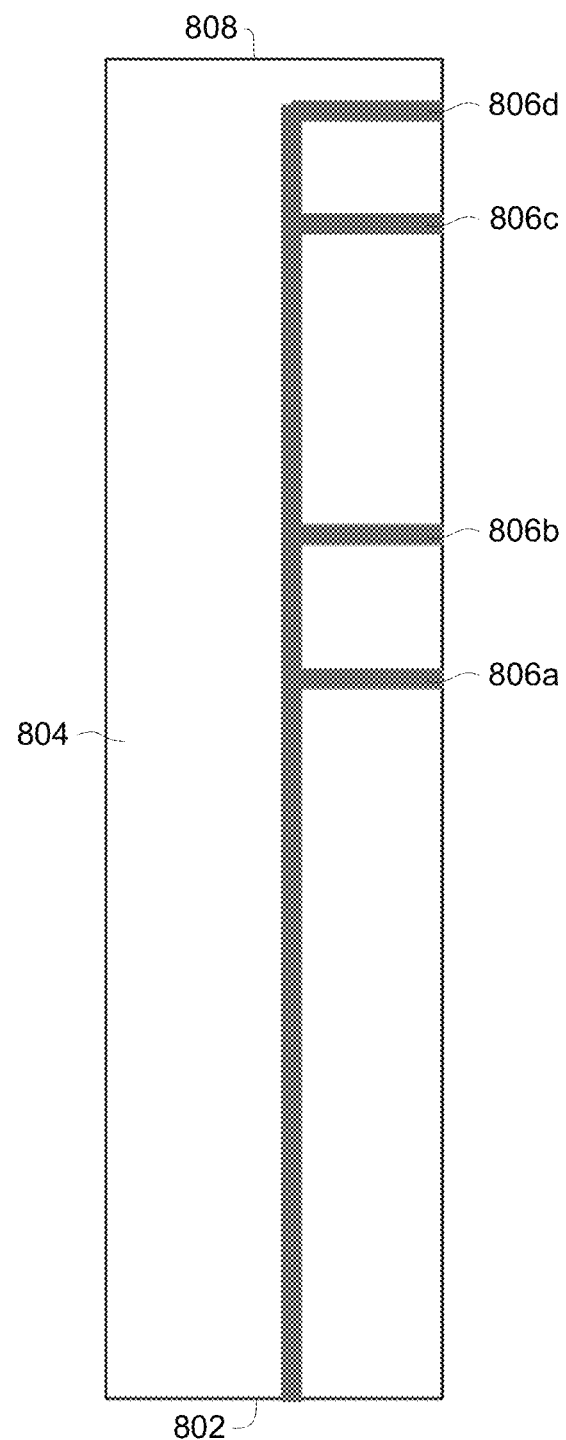
FIG. 8 depicts a schematic top view of an exemplary electrode assembly patch in accordance with aspects of the disclosure.

Although patches have been shown and described as having tabs into which the electrodes may extend, it will be appreciated, that the electrode assembly patch may include only a strip, as shown in FIG. 8, with the electrodes extending into different regions of the strip. For example, as shown in FIG. 8, the electrode assembly patch 800 may include four electrodes (806*a*-806*d*). In some embodiments, the strip 804 may have a uniform thickness between the proximal end 802 and distal end 808 that is larger than that of the strips shown in the other illustrative patches (see, e.g., FIGS. 4A and 6A). As with the above, the distance between the electrodes may be maintained relative to one another via the electrode assembly patch 800 and may be similar to that noted above with respect to the electrode assembly patches with tabs. The length of the electrodes also may be the same as the electrodes extending into the electrode tabs shown in the illustrative patches above.

From the foregoing and with reference to the various figures, those skilled in the art will appreciate that certain modifications can also be made to the present disclosure without departing from the scope of the same. While several aspects of the disclosure have been shown in the figures, it is not intended that the disclosure be limited thereto, as it is intended that the disclosure be as broad in scope as the art will allow and that the specification be read likewise. Therefore, the above description should not be construed as limiting, but merely as exemplifications of particular aspects of the present technology.

In some embodiments, the electrode assembly patch may be configured to form at least a portion of the cannula of the intravascular blood pump. For example, in some embodiments, the electrode assembly patch may form the outer layer of the cannula of the intravascular blood pump. In such embodiments. The electrode assembly patch may be wrapped, rolled, or otherwise placed around a support structure. In one embodiment, the support structure may include one or more strands or coils of a shape-memory material, such as Nitinol. In some embodiments, the cannula may include a multilayered construction including a polyurethane inner layer, a layer formed of the support structure (e.g., Nitinol coils) and an outer layer formed of the electrode assembly patch. In some embodiments, the non-conductive layer of the electrode assembly patch also may comprise polyurethane as non-conductive material.

Exemplary Implementations

As already described, the technology described herein may be implemented in various ways. In that regard, the foregoing disclosure is intended to include, but not be limited to, the systems, methods, and combinations and subcombinations thereof that are set forth in the following categories of exemplary implementations.

Category A:

A1. An electrode assembly patch attachable to an intravascular device, the electrode assembly patch comprising:
a strip extending from a proximal end to a distal end;
a first electrode tab extending outwardly and away from the strip, the first electrode tab configured to provide a current to an ambient fluid;
a second electrode tab spaced from the first electrode tab, the second electrode tab extending outwardly and away from the strip, the second electrode tab configured to measure voltage in the ambient fluid;
a third electrode tab spaced from the second electrode tab, the third electrode tab extending outwardly and away from the strip, the third electrode tab configured to measure voltage in the ambient fluid; and
a fourth electrode tab spaced from the third tab, the fourth electrode tab extending outwardly and away from the strip, the fourth electrode tab configured to provide a current to the ambient fluid.

A2. The electrode assembly patch of A1, wherein the first, second, third, and fourth electrode tabs extend outwardly and away from a first side of the strip in a first direction.

A3. The electrode assembly patch of A2, further comprising:
a first stabilizing tab extending outwardly and away from a second side of the strip in a second direction opposite the first direction; and
a second stabilizing tab spaced from the first stabilizing tab and extending outwardly away from the strip in the second direction.

A4. The electrode assembly patch of A3, wherein the first stabilizing tab is positioned laterally in between the first and second electrode tabs.

A5. The electrode assembly patch of A4, wherein the second stabilizing tab is positioned laterally between the third and fourth electrode tabs.

A6. The electrode assembly patch of one of A1 to A5, wherein the electrode assembly patch is configured to be flexible.

A7. The electrode assembly patch of one of A1 to A6, wherein the electrode assembly patch is configured to have a two-dimensional configuration in an undeployed state and wherein the electrode assembly patch is further configured to have a three-dimensional configuration in a deployed state.

A8. The electrode assembly patch of A1 to A7, wherein each of the first, second, third, and fourth electrode tab includes an electrode extending in the tab.

A9. The electrode assembly patch of A8, wherein the electrode includes one or both of gold or platinum.

A10. The electrode assembly patch of one of A1 to A8, wherein the second tab is spaced apart from the first tab by a first distance, the third tab is spaced apart from the second tab by a second distance, and the fourth tab is spaced apart from the third tab by the first distance.

A11. The electrode assembly patch of A10, wherein the second distance is greater than the first and third distances.

A12. The electrode assembly patch of one of A3 to A11, wherein each of the first, second, third and fourth electrode tabs and each of the first and second stabilizing tabs extend perpendicular to the strip.

A13. The electrode assembly patch of one of A3 to A12, wherein a width of the first stabilizing tab is less than or equal to a first lateral distances between the first and second electrode tabs and wherein a width of the second stabilizing tab is less than or equal to a second lateral distance between the third and fourth electrode tabs.

A14. The electrode assembly patch of one of A1 to A13, wherein the patch includes four layers, each layer having a thickness of 5 µm.

Category B:

B15. A system for determining an admittance or conductance, the system comprising:
an intravascular device configured to be inserted into a patient's heart; and
a flexible electrode assembly patch attached to at least a portion of the intravascular device, wherein the flexible electrode assembly patch includes two or more electrodes configured to determine an admittance and/or conductance.

B16. The system of B15, wherein the flexible electrode assembly patch includes:
a strip extending from a proximal end to a distal end;
a first electrode tab extending outwardly and away from the strip, the first electrode tab configured to provide a current to an ambient fluid;
a second electrode tab spaced from the first electrode tab, the second electrode tab extending outwardly and away from the strip, the second electrode tab configured to measure voltage in the ambient fluid;
a third electrode tab spaced from the second electrode tab, the third electrode tab extending outwardly and away from the strip, the third electrode tab configured to measure voltage in the ambient fluid; and
a fourth electrode tab spaced from the third tab, the fourth electrode tab extending outwardly and away from the strip, the fourth electrode tab configured to provide a current to the ambient fluid.

B17. The system of B16, wherein the first, second, third, and fourth electrode tabs extend outwardly and away from a first side of the strip in a first direction.

B18. The system of B17, further comprising:
a first stabilizing tab extending outwardly and away from a second side of the strip in a second direction opposite the first direction; and
a second stabilizing tab spaced from the first stabilizing tab and extending outwardly away from the strip in the second direction.

B19. The system of B15 to B18, wherein the flexible electrode assembly patch includes a strip having a proximal end and a distal end.

B20. The system of one of B15 to B19, further comprising:
a controller electrically connected to the electrode assembly patch, the controller comprising:
a current source;
a memory; and
one or more processors coupled to the memory and configured to:
provide an alternating current to electrodes of the first electrode tab and the fourth electrode tab;
measure voltages through electrodes of the second electrode tab and the third electrode tab; and
determine an admittance or a conductance based on the measured voltages of the second tab and the third tab.

Category C:

C21. A system for determining an admittance or conductance, the system comprising:
an intravascular device configured to be inserted into a patient's heart; and an electrode assembly patch attached to at least a portion of the intravascular device, wherein the electrode assembly patch includes a multi-layered construction comprising:
a first non-conductive layer configured to adhered to the portion of the intravascular device;
a second layer having one or more wires;
a third non-conductive layer configured to electrically insulate the one or more wires; and
a fourth layer including one or more electrodes.

C22. The system of C21, wherein the first non-conductive layer may be formed from a polymer material configured to be glued, bonded and/or thermoformed to the portion of the intravascular device.

C23. The system of C21 or C22, wherein each of the one or more wires are spaced apart by a non-conductive material.

C24. The system of one of C21 to C23, wherein the one or more wires are formed from a conductive material.

C25. The system of C24, wherein the conductive material includes platinum, gold, silver, and/or copper.

C26. The system of one of C21 to C25, wherein the one or more electrodes in the fourth layer are at least partially exposed.

C27. The system of one of C21 to C26, wherein the multi-layered construction includes four sandwiched layers.

C28. The system of one of C21 to C27, wherein the layers are glued, bonded, and/or thermoformed together.

C29. The system of one of C21 to C28, wherein the electrode assembly patch includes:
a strip extending from a proximal end to a distal end;
a first electrode tab extending outwardly and away from the strip, the first electrode tab configured to provide a current to an ambient fluid;
a second electrode tab spaced from the first electrode tab, the second electrode tab extending outwardly and away from the strip, the second electrode tab configured to measure voltage in the ambient fluid;
a third electrode tab spaced from the second electrode tab, the third electrode tab extending outwardly and away from the strip, the third electrode tab configured to measure voltage in the ambient fluid; and
a fourth electrode tab spaced from the third tab, the fourth electrode tab extending outwardly and away from the strip, the fourth electrode tab configured to provide a current to the ambient fluid.

C30. The system of C29, wherein the first, second, third, and fourth electrode tabs extend outwardly and away from a first side of the strip in a first direction.

C31. The system of C30, further comprising:
a first stabilizing tab extending outwardly and away from a second side of the strip in a second direction opposite the first direction; and
a second stabilizing tab spaced from the first stabilizing tab and extending outwardly away from the strip in the second direction.

C32. The system of one of C31 to C31, wherein the electrode assembly patch includes a strip having a proximal end and a distal end.

C33. The system of C16, further comprising:
a controller electrically connected to the electrode assembly patch, the controller comprising:
a current source;
a memory; and
one or more processors coupled to the memory and configured to:
provide an alternating current to electrodes of the first electrode tab and the fourth electrode tab;
measure voltages through electrodes of the second electrode tab and the third electrode tab; and
determine an admittance or a conductance based on the measured voltages of the second tab and the third tab.

Category D:

D34. A method of forming a system for determining an admittance or conductance, the method comprising:
rolling and/or wrapping a flexible electrode assembly patch to at least a portion of an intravascular device configured to be inserted into a patient's heart; and
attaching the flexible electrode assembly patch to the portion of the intravascular device.

D35. The method of D34, wherein the step of attaching includes, thermoforming the flexible electrode assembly patch to the portion of the intravascular device.

D36. The method of D34 or D35, wherein the flexible electrode assembly patch includes a multi-layered construction.

D37. The method of one of D34 to D36, wherein the flexible electrode assembly patch includes:
a strip extending from a proximal end to a distal end;
a first electrode tab extending outwardly and away from the strip, the first electrode tab configured to provide a current to an ambient fluid;
a second electrode tab spaced from the first electrode tab, the second electrode tab extending outwardly and away from the strip, the second electrode tab configured to measure voltage in the ambient fluid;
a third electrode tab spaced from the second electrode tab, the third electrode tab extending outwardly and away from the strip, the third electrode tab configured to measure voltage in the ambient fluid; and
a fourth electrode tab spaced from the third tab, the fourth electrode tab extending outwardly and away from the strip, the fourth electrode tab configured to provide a current to the ambient fluid.

D38. The method of D37, wherein the first, second, third, and fourth electrode tabs extend outwardly and away from a first side of the strip in a first direction.

D39. The method of D38, wherein the flexible electrode assembly patch further comprises:
a first stabilizing tab extending outwardly and away from a second side of the strip in a second direction opposite the first direction; and
a second stabilizing tab spaced from the first stabilizing tab and extending outwardly away from the strip in the second direction.

D40. The method of one of D34 to D39, wherein the flexible electrode assembly patch includes a two-dimensional configuration before the flexible electrode assembly patch is rolled and/or wrapped onto the intravascular device.

Category E:

E41. An intravascular blood pump system, comprising:
An intravascular blood pump configured to pump blood through a cannula from a blood inlet to a blood outlet;
an electrode assembly coupled to at least a portion of the cannula, the electrode assembly comprising:
a strip extending from a proximal end to a distal end;
a first tab extending perpendicularly away from the strip, the first tab having an electrode configured to provide a current to an ambient fluid;
a second tab positioned distal of the first tab and extending perpendicularly away from the strip, the second tab configured to measure voltage in the ambient fluid;

a third tab positioned distal of the second tab and extending perpendicularly away from the strip, the third tab configured to measure voltage in the ambient fluid; and a fourth tab positioned distal of the third tab and extending perpendicularly away from the strip, the fourth tab configured to provide a current to the ambient fluid;

a controller electrically connected to the electrode assembly, the controller comprising:

a current source;

a memory; and one or more processors coupled to the memory and configured to:

provide an alternating current to the electrodes of the first tab and the fourth tab;

measure voltages through the electrodes of the second tab and the third tab; and determine an admittance or a conductance based on the measured voltages of the second tab and the third tab.

E42. The system of E41, wherein the second tab is spaced apart distally from the first tab by a first distance, the third tab is spaced apart distally from the second tab by a second distance, and the fourth tab is spaced apart distally from the third tab by the first distance.

E43. The system of E42, wherein the electrode assembly further comprises:

a fifth tab positioned distal of the first tab and proximal of the second tab, and extending perpendicularly away from the strip in an opposite direction from the first tab and the second tab; and a sixth tab positioned distal of the third tab and proximal of the fourth tab, and extending perpendicularly away from the strip in an opposite direction from the third tab and the fourth tab.

E44. The system of E43, wherein a width of the fifth tab and a width of the sixth tab are configured to be less than or equal to the first distance.

E45. The system of E44, wherein the first distance is 3 mm.

E46. The system of E45, wherein the width of the fifth tab and the width of the sixth tab are 2.5 mm.

E47. The system of E45, wherein the second distance is 10 mm.

E48. The system of E42, wherein the electrode assembly further comprises:

a fifth tab positioned proximal of the first tab, and extending perpendicularly away from the strip in an opposite direction from the first tab and the second tab; and a sixth tab positioned distal of the second tab and proximal of the third tab, and extending perpendicularly away from the strip in an opposite direction from the third tab and the fourth tab.

E49. The system of claim E48, wherein the first distance is 3 mm.

E50. The system of E49, wherein a width of the fifth tab and a width of the sixth tab is 3 mm.

E51. The system of E49, wherein the second distance is 10 mm.

E52. The system of E41, wherein the electrode assembly is configured to be flexible.

E53. The system of E41, wherein the electrodes of the first tab, second tab, third tab, and fourth tab comprise one or both of gold or platinum.

E54. The system of E41, wherein the electrode assembly comprises four layers, each layer having a thickness of 5 μm.

E55. The system of E41, wherein the current source is configured to provide a substantially constant alternating current of 10 and 100 μA at 20 kHz.

Category F:

F56. A system for determining admittance or conductance, comprising:

An intravascular device configured to be inserted into a patient's heart;

an electrode assembly coupled to at least a portion of the intravascular device, the electrode assembly comprising:

a strip extending from a proximal end to a distal end;

a first tab extending perpendicularly away from the strip, the first tab having an electrode configured to provide a current to an ambient fluid;

a second tab positioned distal of the first tab and extending perpendicularly away from the strip, the second tab configured to measure voltage in the ambient fluid;

a third tab positioned distal of the second tab and extending perpendicularly away from the strip, the third tab configured to measure voltage in the ambient fluid; and a fourth tab positioned distal of the third tab and extending perpendicularly away from the strip, the fourth tab configured to provide a current to the ambient fluid;

a controller electrically connected to the electrode assembly, the controller comprising:

a current source;

a memory; and one or more processors coupled to the memory and configured to:

provide an alternating current to the electrodes of the first tab and the fourth tab;

measure voltages through the electrodes of the second tab and the third tab; and determine an admittance or a conductance based on the measured voltages of the second tab and the third tab.

F57. The system of F56, wherein the second tab is spaced apart distally from the first tab by a first distance, the third tab is spaced apart distally from the second tab by a second distance, and the fourth tab is spaced apart distally from the third tab by the first distance.

F58. The system of F57, wherein the electrode assembly further comprises:

a fifth tab positioned distal of the first tab and proximal of the second tab, and extending perpendicularly away from the strip in an opposite direction from the first tab and the second tab; and a sixth tab positioned distal of the third tab and proximal of the fourth tab, and extending perpendicularly away from the strip in an opposite direction from the third tab and the fourth tab.

F59. The system of F58, wherein a width of the fifth tab and a width of the sixth tab are configured to be less than or equal to the first distance.

F60. The system of F59, wherein the first distance is 3 mm.

F61. The system of F60, wherein the width of the fifth tab and the width of the sixth tab are 2.5 mm.

F62. The system of F60, wherein the second distance is 10 mm.

F63. The system of F57, wherein the electrode assembly further comprises:

a fifth tab positioned proximal of the first tab, and extending perpendicularly away from the strip in an opposite direction from the first tab and the second tab; and a sixth tab positioned distal of the second tab and proximal of the third tab, and extending perpendicularly away from the strip in an opposite direction from the third tab and the fourth tab.

F64. The system of F63, wherein the first distance is 3 mm.

F65. The system of F64, wherein a width of the fifth tab and a width of the sixth tab is 3 mm.

F66. The system of F64, wherein the second distance is 10 mm.

F67. The system of F56, wherein the electrode assembly is configured to be flexible.

F68. The system of F56, wherein the electrodes of the first tab, second tab, third tab, and fourth tab comprise one or both of gold or platinum.

F69. The system of F56, wherein the electrode assembly comprises four layers, each layer having a thickness of 5 μm.

F70. The system of F56, wherein the current source is configured to provide a substantially constant alternating current of 10 and 100 μA at 20 kHz.

The invention claimed is:

1. An electrode assembly patch comprising:
a strip extending from a proximal end to a distal end;
a first electrode tab extending outwardly and away from the strip, the first electrode tab configured to provide a current to an ambient fluid;
a second electrode tab spaced from the first electrode tab, the second electrode tab extending outwardly and away from the strip, the second electrode tab configured to measure voltage in the ambient fluid;
a third electrode tab spaced from the second electrode tab, the third electrode tab extending outwardly and away from the strip, the third electrode tab configured to measure voltage in the ambient fluid; and
a fourth electrode tab spaced from the third electrode tab, the fourth electrode tab extending outwardly and away from the strip, the fourth electrode tab configured to provide a current to the ambient fluid,
wherein the strip and the first, second, third, and fourth electrode tabs are configured to attach to an intravascular blood pump.

2. The electrode assembly patch of claim 1, wherein the first, second, third, and fourth electrode tabs extend outwardly and away from a first side of the strip in a first direction.

3. The electrode assembly patch of claim 1, wherein the electrode assembly patch is configured to be flexible.

4. The electrode assembly patch of claim 1, wherein the electrode assembly patch is configured to have a two-dimensional configuration in an undeployed state, and wherein the electrode assembly patch is further configured to have a three-dimensional configuration in a deployed state.

5. The electrode assembly patch of claim 1, wherein each one of the first, second, third, and fourth electrode tabs includes an electrode extending in the tab.

6. The electrode assembly patch of claim 5, wherein each one of the electrodes includes gold or platinum.

7. The electrode assembly patch of claim 1, wherein the second electrode tab is spaced apart from the first electrode tab by a first distance, the third electrode tab is spaced apart from the second electrode tab by a second distance, and the fourth electrode tab is spaced apart from the third electrode tab by a third distance.

8. The electrode assembly patch of claim 7, wherein the second distance is greater than the first and third distances.

9. The electrode assembly patch of claim 1, wherein the electrode assembly patch includes four layers, each layer having a thickness of 5 μm.

10. A system comprising:
the intravascular blood pump of claim 1; and
the electrode assembly patch of claim 1 attached to at least a portion of the intravascular blood pump.

11. The system of claim 10, further comprising:
a controller electrically connected to the electrode assembly patch, the controller comprising:
a current source;
a memory; and
one or more processors coupled to the memory and configured to:
provide an alternating current to electrodes of the first electrode tab and the fourth electrode tab;
measure voltages through electrodes of the second electrode tab and the third electrode tab; and
determine an admittance or a conductance based on the measured voltages of the second electrode tab and the third electrode tab.

12. The system of claim 11, wherein the current source is configured to provide a substantially constant alternating current of 10 and 100 μA at 20 KHz.

13. An electrode assembly patch attachable to an intravascular device, the electrode assembly patch comprising:
a strip extending from a proximal end to a distal end;
a first electrode tab extending outwardly and away from the strip, the first electrode tab configured to provide a current to an ambient fluid;
a second electrode tab spaced from the first electrode tab, the second electrode tab extending outwardly and away from the strip, the second electrode tab configured to measure voltage in the ambient fluid;
a third electrode tab spaced from the second electrode tab, the third electrode tab extending outwardly and away from the strip, the third electrode tab configured to measure voltage in the ambient fluid;
a fourth electrode tab spaced from the third electrode tab, the fourth electrode tab extending outwardly and away from the strip, the fourth electrode tab configured to provide a current to the ambient fluid;
a first stabilizing tab; and
a second stabilizing tab spaced from the first stabilizing tab,
wherein the first, second, third, and fourth electrode tabs extend outwardly and away from a first side of the strip in a first direction, and
wherein the first and second stabilizing tabs extend outwardly and away from a second side of the strip in a second direction opposite the first direction.

14. The electrode assembly patch of claim 13, wherein the first stabilizing tab is positioned laterally in between the first and second electrode tabs.

15. The electrode assembly patch of claim 14, wherein the second stabilizing tab is positioned laterally between the third and fourth electrode tabs.

16. The electrode assembly patch of claim 13, wherein each one of the first, second, third, and fourth electrode tabs and each one of the first and second stabilizing tabs extend perpendicular to the strip.

17. The electrode assembly patch of claim 13, wherein a width of the first stabilizing tab is less than or equal to a first lateral distance between the first and second electrode tabs, and wherein a width of the second stabilizing tab is less than or equal to a second lateral distance between the third and fourth electrode tabs.

18. The electrode assembly patch of claim 13, wherein the second electrode tab is spaced apart distally from the first electrode tab by a first distance, the third electrode tab is spaced apart distally from the second electrode tab by a second distance, and the fourth electrode tab is spaced apart distally from the third electrode tab by the first distance.

19. The electrode assembly patch of claim 18, wherein the first stabilizing tab is positioned distal of the first electrode tab and proximal of the second electrode tab, and wherein the second stabilizing tab is positioned distal of the third electrode tab and proximal of the fourth electrode tab.

20. The electrode assembly patch of claim 19, wherein a width of the first stabilizing tab and a width of the second stabilizing tab are configured to be less than or equal to the first distance.

21. The electrode assembly patch of claim 18, wherein the first stabilizing tab is positioned proximal of the first electrode tab, wherein the second stabilizing tab is positioned distal of the second electrode tab and proximal of the third electrode tab, and wherein the first and second stabilizing tabs extend perpendicularly away from the strip in the second direction.

22. A method comprising:
   attaching an electrode assembly patch to at least a portion of an intravascular blood pump, wherein the electrode assembly patch comprises:
   a strip extending from a proximal end to a distal end;
   a first electrode tab extending outwardly and away from the strip, the first electrode tab configured to provide a current to an ambient fluid;
   a second electrode tab spaced from the first electrode tab, the second electrode tab extending outwardly and away from the strip, the second electrode tab configured to measure voltage in the ambient fluid;
   a third electrode tab spaced from the second electrode tab, the third electrode tab extending outwardly and away from the strip, the third electrode tab configured to measure voltage in the ambient fluid; and
   a fourth electrode tab spaced from the third electrode tab, the fourth electrode tab extending outwardly and away from the strip, the fourth electrode tab configured to provide a current to the ambient fluid.

23. The method of claim 22, wherein each one of the first, second, third, and fourth electrode tabs includes an electrode extending in the tab.

24. The method of claim 22, wherein the electrode assembly patch includes four layers, each layer having a thickness of 5 μm.

* * * * *